(12) United States Patent
Kim et al.

(10) Patent No.: US 11,039,525 B2
(45) Date of Patent: Jun. 15, 2021

(54) CARTRIDGE-TYPE X-RAY SOURCE APPARATUS AND X-RAY EMISSION APPARATUS USING SAME

(71) Applicants: VATECH Co., Ltd., Gyeonggi-do (KR); VATECH EWOO Holdings Co., Ltd., Gyeonggi-do (KR)

(72) Inventors: Tae Woo Kim, Gyeonggi-do (KR); In Jae Baek, Gyeonggi-do (KR); Soo Bong Lee, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 737 days.

(21) Appl. No.: 15/301,469

(22) PCT Filed: Apr. 1, 2015

(86) PCT No.: PCT/KR2015/003266
§ 371 (c)(1),
(2) Date: Oct. 3, 2016

(87) PCT Pub. No.: WO2015/152640
PCT Pub. Date: Oct. 8, 2015

(65) Prior Publication Data
US 2017/0111984 A1    Apr. 20, 2017

(30) Foreign Application Priority Data

Apr. 1, 2014    (KR) .................. 10-2014-0038499
Sep. 12, 2014   (KR) .................. 10-2014-0121083
(Continued)

(51) Int. Cl.
*H01J 35/00*    (2006.01)
*H05G 1/04*    (2006.01)
(Continued)

(52) U.S. Cl.
CPC ............ *H05G 1/04* (2013.01); *G21K 1/02* (2013.01); *H01J 35/16* (2013.01); *H01J 35/165* (2013.01);
(Continued)

(58) Field of Classification Search
CPC .................. H01J 2235/023; H01J 35/165
See application file for complete search history.

(56) References Cited

U.S. PATENT DOCUMENTS

| 4,920,554 A | 4/1990 | Gabbay et al. |
| 2010/0036233 A1 | 2/2010 | Zhu et al. |

(Continued)

FOREIGN PATENT DOCUMENTS

| CN | 1509492 A | 6/2004 |
| DE | 497356 C | 5/1930 |

(Continued)

OTHER PUBLICATIONS

Korean Intellectual Property Office, International Search Report of International Application No. PCT/KR2015/003266, dated Jul. 21, 2015.

(Continued)

*Primary Examiner* — Dani Fox
(74) *Attorney, Agent, or Firm* — IP Legal Services, LLC

(57) ABSTRACT

Disclosed are a cartridge-type X-ray source apparatus and an X-ray emission apparatus using the same. The X-ray source includes: a cathode electrode provided with an electron emission source by using a nanostructure; an anode electrode having a target emitting X-rays by electron collision; and a housing forming an external appearance, and exposing a cathode electrode terminal connected to the cathode electrode and an anode electrode terminal connected to the anode electrode to an outside thereof, wherein the cathode electrode terminal and the anode electrode terminal differ (Continued)

from each other in at least one of exposure direction, height, size, and shape.

17 Claims, 15 Drawing Sheets

(30) Foreign Application Priority Data

Sep. 12, 2014 (KR) ........................ 10-2014-0121099
Sep. 12, 2014 (KR) ........................ 10-2014-0121145

(51) Int. Cl.
 *H01J 35/16* (2006.01)
 *G21K 1/02* (2006.01)
 *A61B 6/14* (2006.01)
 *A61B 6/00* (2006.01)

(52) U.S. Cl.
 CPC ............. *A61B 6/145* (2013.01); *A61B 6/4411* (2013.01); *H01J 2235/023* (2013.01); *H01J 2235/062* (2013.01); *H01J 2235/166* (2013.01)

(56) References Cited

U.S. PATENT DOCUMENTS

| 2011/0188635 A1 | 8/2011 | Cho et al. |
| 2011/0245951 A1 | 10/2011 | Gantes |
| 2011/0255664 A1 | 10/2011 | Ueda et al. |

FOREIGN PATENT DOCUMENTS

| JP | 07-029487 A | 1/1995 |
| JP | 2006-086001 A | 3/2006 |
| JP | 2012-079449 A | 4/2012 |
| KR | 10-2006-0077549 A | 7/2006 |
| KR | 10-2007-0038849 A | 4/2007 |
| KR | 10-2011-0090357 A | 8/2011 |

OTHER PUBLICATIONS

Korean Intellectual Property Office, Written Opinion of the International Searching Authority of International Application No. PCT/KR2015/003266, dated Jul. 21, 2015.
The State Intellectual Property Office of People's Republic of China, Office Action of corresponding CN Patent Application No. 201580028998.9, dated Aug. 22, 2017.
European Patent Office, Extended European Search Report of corresponding EP Patent Application No. 15772475.8, dated Nov. 3, 2017.

CARTRIDGE-TYPE X-RAY SOURCE APPARATUS AND X-RAY EMISSION APPARATUS USING SAME

CROSS REFERENCE TO RELATED APPLICATIONS

This application is a National Stage Patent Application of PCT International Patent Application No. PCT/KR2015/003266 (filed on Apr. 1, 2015) under 35 U.S.C. § 371, which claims priority to Korean Patent Application Nos. 10-2014-0038499 (filed on Apr. 1, 2014), 10-2014-0121099 (filed on Sep. 12, 2014), 10-2014-0121145 (filed on Sep. 12, 2014) and 10-2014-0121083 (filed on Sep. 12, 2014), the teachings of which are incorporated herein in their entireties by reference.

TECHNICAL FIELD

The present invention relates generally to a cartridge-type X-ray source using a nanostructure and an X-ray emission apparatus using the same. More particularly, the present invention relates to a cartridge-type X-ray source including a cathode electrode having an electron emission source using a nanostructure, and an anode electrode corresponding to the cathode electrode with terminals connected to the electrodes being exposed outside a body or housing, and relates to an X-ray emission apparatus including the same.

BACKGROUND ART

In general, in an X-ray source used for disease diagnosis in medical institutions, a hot cathode made of tungsten material is used as an electron emission source for generating X-rays, wherein a tungsten filament is heated by applying a high voltage thereto so as to emit electrons, and the emitted electrons are bombarded against a target of an anode electrode, thereby generating X-rays.

However, a conventional hot cathode X-ray source based on a tungsten filament is problematic in that much energy is required to generate electrons, and since electrons to be generated are randomly emitted from a tungsten surface having a spiral structure, electrons that are bombarded against a target of an anode electrode to generate X-rays are below 5% of the emitted electrons, so efficiency is extremely low. The conventional X-ray source is further problematic in that an interval for a period of time is required to heat and cool the tungsten filament, and since it is difficult to emit X-rays in a pulse shape, X-rays are overly irradiated, so use of the conventional X-ray source is limited in dental treatment, such as a dental implant checking.

Recently, to solve the above problems of the conventional hot cathode X-ray source, an X-ray source using a nanostructure as a cold cathode electron emission source, particularly, an X-ray source based on a carbon nanotube has been actively researched. The X-ray source using a carbon nanotube, unlike the conventional hot cathode X-ray source based on a tungsten filament, employs an electric field emission type as an electron emission mechanism, which differs from the conventional thermionic emission type.

When compared to the hot cathode X-ray source based on a tungsten filament, the X-ray source based on a carbon nanotube is capable of emitting electrons by applying a low voltage, and since electrons to be emitted are emitted along a longitudinal direction of the carbon nanotube, the electrons have good directivity toward a target of an anode electrode, so efficiency in X-ray emission is very high. Further, since it is easy to emit X-rays in a pulse shape, it is possible to obtain a moving image as well as to a radiograph, with a low dose of X-ray radiation, so usability of the X-ray source based on a carbon nanotube is very high in dental treatment, such as a dental implant check.

However, the X-ray source based on a carbon nanotube is problematic in that the inside of the apparatus, in which an electron emission source is accommodated, is required to be in a high vacuum state, but it is difficult to maintain a high vacuum state due to gassing inside the apparatus, and accordingly the apparatus has a short life. The X-ray source based on a carbon nanotube is further problematic in that insulating effect is low, life becomes short in accordance with deterioration of insulation reliability, and since an additional component, such as a surge protector, is required for perfect insulation, the X-ray source based on a carbon nanotube is uneconomical in terms of size or cost.

DISCLOSURE

Technical Problem

Accordingly, the present invention has been made keeping in mind the above problems occurring in the related art, and the present invention is intended to propose an X-ray source using a nanostructure, the X-ray source configured such that insulating effect is improved using a silicon compound including silicon rubber as an insulator, and thereby the X-ray source has a long life and reliability thereof is improved.

The present invention is further intended to propose a cartridge-type X-ray source and an X-ray emission apparatus using the same, wherein the cartridge-type X-ray source is replaceable with ease if necessary, by configuring an X-ray source using a nanostructure such that terminals of a cathode electrode and an anode electrode thereof are able to be electrically connected to connection terminals outside the X-ray source.

Technical Solution

In order to achieve the above object, according to one aspect of the present invention, there is provided an X-ray emission apparatus including: a main body including a cartridge mounting part configured to allow an X-ray source to be replaceably mounted thereto and to generate X-rays from the X-ray source mounted on the cartridge mounting part to be irradiated onto an X-ray irradiation path, wherein the X-ray source includes: a cathode electrode provided with an electron emission source using a nanostructure; an anode electrode having a target emitting X-rays by electron collision; and a housing forming an external appearance, and exposing a cathode electrode terminal connected to the cathode electrode and an anode electrode terminal connected to the anode electrode to an outside thereof, wherein the cathode electrode terminal and the anode electrode terminal differ from each other in at least one of exposure direction, height, size, and shape, and the cartridge mounting part includes first and second connection terminals brought into physical contact with the anode electrode terminal and the cathode electrode terminal.

The anode electrode terminal and the cathode electrode terminal may be exposed outside either toward a same direction with the height thereof being different from each other, or toward different directions.

Each of an outer surface of the housing and the cartridge mounting part may be provided with at least one guide member corresponding to each other.

The main body may be provided with the cartridge mounting part in plural, each of which the X-ray source is mounted to.

Here, the main body may include a rotary loader moving one of the plurality of X-ray sources toward the X-ray irradiation path. Further, the main body may include a multi-collimator irradiating X-rays generated from the plurality of X-ray sources onto the X-ray irradiation path.

In order to achieve the above object, according to another aspect of the present invention, there is further provided a cartridge-type X-ray source including: a cathode electrode provided with an electron emission source using a nanostructure; an anode electrode having a target emitting X-rays by electron collision; and a housing forming an external appearance, and exposing a cathode electrode terminal connected to the cathode electrode and an anode electrode terminal connected to the anode electrode to an outside thereof, wherein the cathode electrode terminal and the anode electrode terminal differ from each other in at least one of exposure direction, height, size, and shape, wherein the X-ray source is replaceably mounted to an X-ray emission apparatus in a cartridge-type manner.

The anode electrode terminal and the cathode electrode terminal may be exposed outside either toward a same direction with the heights thereof being different from each other, or exposed toward different directions.

Each of an outer surface of the housing and the X-ray emission apparatus may be provided with at least one guide member corresponding to each other.

Advantageous Effects

According to the present invention having the above-described characteristics, there is provided a cartridge-type X-ray source capable of being easily replaceable if necessary, by configuring an X-ray source using a nanostructure such that terminals of a cathode electrode and an anode electrode thereof are able to be electrically connected to connection terminals outside the X-ray source. The present invention is advantageous in that by configuring an X-ray source having a short lift of an X-ray emission apparatus to be in a replaceable cartridge-type, it is possible to reduce the maintenance workload of the X-ray emission apparatus.

The present invention is further advantageous in that in the cartridge-type X-ray source and a cartridge mounting part of a main body of the X-ray emission apparatus, through efficient connection between an electrode terminal structure and a connection terminal structure, make it is possible to realize precise and stable mechanical engagement and electrical connection between the cartridge-type X-ray source and the X-ray emission apparatus.

MODE FOR INVENTION

Reference will now be made in greater detail to an exemplary embodiment of the present invention, an example of which is illustrated in the accompanying drawings. It should be understood that the embodiment of the present invention may be changed to a variety of embodiments and the scope and spirit of the present invention are not limited to the embodiment described hereinbelow. The embodiment of the present invention described hereinbelow is provided for allowing those skilled in the art to more clearly comprehend the present invention.

Figure 1:
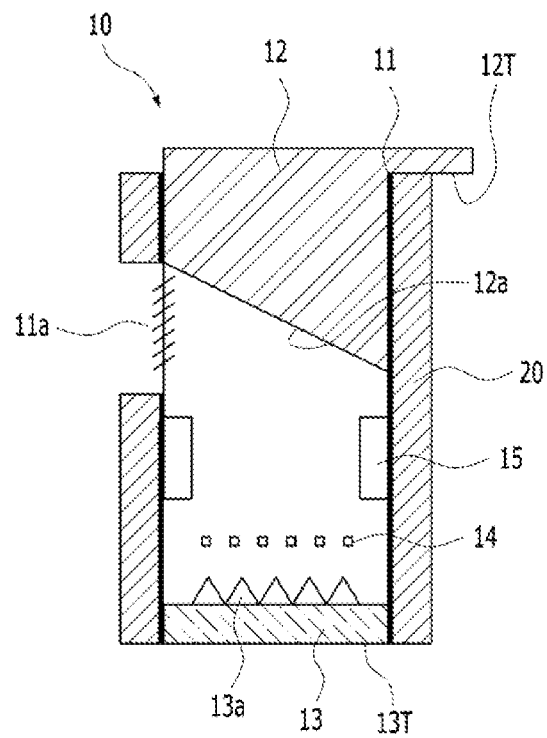
FIG. 1 is a schematic sectional view showing an X-ray source using a nanostructure according to an embodiment of the present invention.

Referring to FIG. 1, according to an embodiment of the present invention, an X-ray source 10 using a nanostructure (hereinbelow, referred to as an X-ray source) includes: a tubular body 11; an anode electrode 12 provided at a first end of the body 11, and having a target surface 12a for generating X-rays; and a cathode electrode 13 provided at a second end of the body 11, and formed with a nanostructure 13a on a surface facing the target surface 12a, wherein the anode electrode 12 and at least a portion of the cathode electrode 13 are connected to connection terminals outside the X-ray source 10 toward a same direction with the height thereof being different from each other.

In other words, according to the embodiment of the present invention, the X-ray source 10 is configured such that electrons that are field emitted from the nanostructure 13a by a voltage difference between the cathode electrode 13 and the anode electrode 12 are bombarded against the target surface 12a of the anode electrode 12, thereby emitting X-rays to a window 11a of the body 11.

The body 11 forms an external appearance of the X-ray source, and may be provided with the window 11a at a portion of a side surface thereof for allowing X-rays emitted from the target surface 12a of the anode electrode 12 to be irradiated outside. The body is in a tubular shape, and defines a vacuum area separated from the outside by surrounding outer surfaces of the anode electrode 12, the cathode electrode 13, a gate electrode 14, and a focusing electrode 15 to be described hereinafter.

The body 11 may be made of an insulating material, such as glass or silicon, and thereby the body 11 serves to primarily insulate the X-ray source 10. Further, the window 11a may be made of either one or an alloy of beryllium (Be), aluminum (Al), magnesium (Mg), aluminum nitride (AlN), aluminum-beryllium alloy (AlBe), silicon oxide (SixOy), and titanium (Ti).

According to the embodiment of the present invention, at least a portion of the anode electrode 12 extends to the outside of an outer circumference of the body 11 so as to be exposed outside toward the same direction as the cathode electrode 13, and the exposed portion forms an anode electrode terminal 12T. However, a configuration of the anode electrode 12 and the anode electrode terminal 12T is not limited to the above configuration. For example, an additional anode terminal electrode that is electrically connected to the anode electrode 12 may be provided, which will be described hereinafter.

The anode electrode 12 serves to produce a voltage difference between the anode electrode and the cathode electrode 13, and also serves as a target that emits X-rays by collision of the electrons emitted from the nanostructure 13a. To achieve this, the anode electrode 12 is provided with the target surface 12a on a surface thereof facing an inside of the body 11, the target surface allowing the electrons emitted from the nanostructure 13a to be bombarded thereagainst. The target surface 12a may be in an inclined-shape that is configured to be close to the cathode electrode 13 as the target surface is away from the window 11a. However, without being limited thereto, various changes in the shape of the anode electrode 12 may be made according to a shape of an area that X-rays are emitted from.

The target surface 12a of the anode electrode 12 may be a target film made of a target material constituted by tungsten (W), copper (Cu), molybdenum (Mo), cobalt (Co), chromium (Cr), iron (Fe), silver (Ag), tantalum (Ta), or yttrium (Y). Instead of providing the anode electrode 12 with the additional target film, the anode electrode 12 itself may be made of a target material constituted by tungsten (W), copper (Cu), molybdenum (Mo), cobalt (Co), chromium (Cr), iron (Fe), silver (Ag), tantalum (Ta), or yttrium (Y). When the electrons emitted from the nanostructure 13a are bombarded against the target surface 12a, X-rays are generated and emitted.

The cathode electrode 13 is disposed at a second end inside the body 11 so as to face the anode electrode 12, and is provided with the nanostructure 13a emitting electrons, on a surface facing the anode electrode 12. In the embodiment, at least a portion of the cathode electrode 13 is exposed outside to form a cathode electrode terminal 13T, and thereby having a structure exposed toward the same direction as the above described anode electrode terminal 12T. However, without being limited thereto, by providing an additional cathode terminal electrode that is electrically connected to the cathode electrode 13, a portion of the cathode terminal electrode may be exposed toward the same direction as the anode electrode terminal 12T, and reference thereto will be made in connection with an embodiment to be described hereinafter. In other words, the cathode electrode terminal 13T may belong to a portion of the cathode electrode 13, or may belong to a portion of an additional terminal electrode that is electrically connected to the cathode electrode 13.

The cathode electrode 13 may be constituted by at least one of a doped silicon (Si) wafer, and a high-conductive metal or alloy; and the nanostructure 13a may be constituted by at least one of a carbon nanotube, carbon nanofibers, a nanowire, a graphene, and a nanodiamond. Herein, up to now, in the case where a carbon nanotube is used for a nanostructure constituting an electron emission source, it is known that electron emission efficiency is high.

The carbon nanotube constituting the nanostructure 13a may be provided by being grown directly on an upper portion of the cathode electrode 13, or may be provided by plastic deformation after applying a carbon nanotube paste on the upper portion of the cathode electrode 13. In the case of directly growing the carbon nanotube, a process where a catalyst metal pattern is formed on a surface of the cathode electrode 13, and a chemical vapor deposition processing may be included. The nanostructure 13a, as an electron emission source, may be provided by growing the carbon nanotube thereon after a sharp protruding tip is formed on the cathode electrode 13.

Further, the X-ray source 10 according to the embodiment may be configured to be a three electrode structure by adding a gate electrode 14 between the cathode electrode 13 and the anode electrode 12, or may be configured to be a four electrode structure by adding at least one focusing electrode 15 between the gate electrode 14 and the anode electrode 12. The X-ray source 10 may further include a getter electrode to remove gas generated inside the body 11 of the X-ray source and to maintain a high vacuum state inside the body 11.

As shown in the drawings, the gate electrode 14 is disposed close to the nanostructure 13a of the cathode electrode 13. A predetermined voltage that is higher than that of the cathode electrode 13 and lower than that of the anode electrode 12 is applied to the gate electrode 14 so as to generate an electron field between the gate electrode and the nanostructure 13a. Thereby, the gate electrode induces the nanostructure 13a to emit electrons, and controls the amount of electron emission. The gate electrode 14 may be in the form of a meshed metal grid. As the gate electrode 14, a metal plate having a plurality of holes corresponding to each of the nanostructure 13a may be provided.

The focusing electrode 15 serves to focus the electrons emitted from the nanostructure 13a by generating a predetermined electric field, which is similar to an optical lens for focusing light in the optical system. The focusing electrode 15 is in a ring shape, wherein the focusing electrode 15 may be made a metal material constituted by aluminum (Al) or tungsten (W), and the surface thereof may be made of an insulating material constituted by alumina ($Al_2O_3$) or tungsten oxide (WO3). However, without being limited thereto, various changes in the shape and material of the focusing electrode 15 may be made.

Further, to be insulated from the cathode electrode 13, each of the gate electrode 14 and the focusing electrode 15 may be connected to the outside by penetrating through the cathode electrode 13, or may be exposed to the outside through an additional terminal provided outside the cathode electrode 13, toward the same direction as the cathode electrode terminal 13T. This manner may be applied to the case where the cathode terminal electrode is provided separated from the cathode electrode 13.

The X-ray source 10 of the present invention may further include an insulator 20 surrounding the outer surface of the body 11, wherein when the body 11 primarily insulates the apparatus; the insulator 20 secondarily insulates the same, thereby maximizing insulating effect. The insulator 20 may be made of a silicon compound, wherein the silicon compound may be a compound by mixing silicon rubber with one selected from the group constituted by ethylene, polyethylene, polypropylene, polyurethane, polyester, polyvinyl chloride, polyvinylidene flurioride, polytetrafluorethylene, alpha olefin copolymer, ethylene-propylenediene copolymer, ethylene fluoride-propylene copolymer, and ethylene-tetrafluorethylene copolymer.

In the case where the nanostructure 13a is used as the electron emission source of the X-ray source 10, and particularly in the case of using the carbon nanotube as the electron emission source, since the energy level of the emitted electrons is low, a high voltage is applied between the cathode electrode 13 and the anode electrode 12 in order to sufficiently accelerate the electrons until the electrons are bombarded against the target surface 12a of the anode electrode 12. In order to stably maintain the large potential difference, it is important to use a material having high dielectric strength, as an insulator. In the case of the insulator of the present invention, which is made of the silicon compound, it is possible to stably maintain a high voltage difference between the cathode electrode and the anode electrode, and thereby it is possible to improve stability and reliability of the X-ray source.

Figure 2:
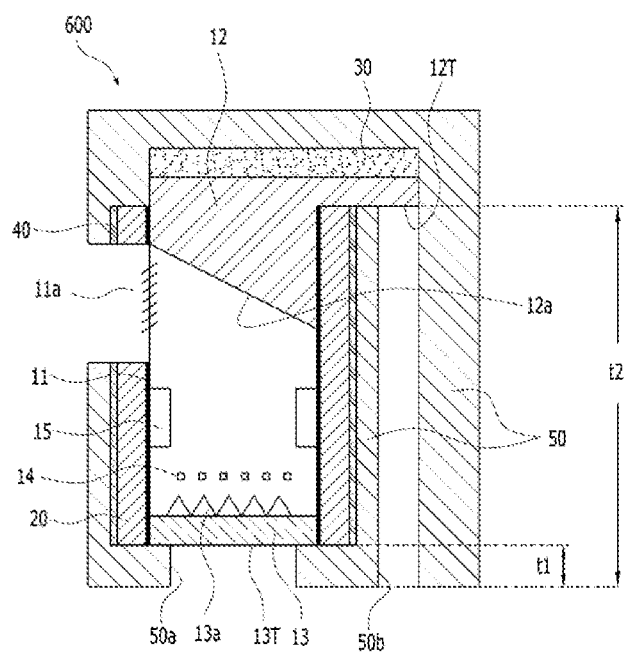
FIG. 2 is a schematic sectional view showing a cartridge-type X-ray source according to an embodiment of the present invention.

FIG. 2 is a schematic sectional view showing a cartridge-type X-ray source according to an embodiment of the present invention. The cartridge-type X-ray source 600 according to the embodiment of the present invention may further include a heat conductor 30, a shielding layer 40, and a housing 50 in addition to the X-ray source 10 according to the embodiment of FIG. 1.

The heat conductor 30 is disposed to be in contact with a side of the anode electrode 12, and preferably, with an upper portion thereof, and serves to dissipate heat that is generated from the anode electrode 12 as the electrons are bombarded against the target surface 12a, to the outside. However, without being limited thereto, when an additional anode terminal electrode is provided outside the anode electrode 12, the heat conductor may be disposed to be in contact with an upper portion of the anode terminal electrode.

The shielding layer 40 is provided at a portion of an outer surface or the entire outer surface of the insulator 20 except the window 11a, and may be made of one of lead, tungsten, and a composite sheet of silicon polymer and barium sulfate, but not limited thereto. By providing the shielding layer 40, it is possible to prevent X-rays from being emitted to other areas except the window 11a.

The housing 50 is made of an insulating material, such as ceramic, synthetic resin, silicon, or the like, and forms an external appearance of the cartridge-type X-ray source 600 according to the present invention by surrounding both the X-ray source and the shielding layer 40.

The housing 50 is provided with a first hole 50a and a second hole 50b for respectively allowing the cathode electrode terminal 13T and the anode electrode terminal 12T to be exposed. The first and the second holes allow the cathode electrode terminal 13T and the anode electrode terminal 12T to be exposed toward a same direction with the height thereof being different from each other. In other words, the cathode electrode terminal 13T is exposed to the outside through the first hole 50a of the housing 50; and the anode electrode terminal 12T is exposed to the outside through second hole 50b that is formed in the housing 50 in the same direction as the first hole 50a with a depth thereof being different from the first hole 50a. Here, assuming that the depth of the first hole 50a is t1, and the depth of the second hole 50b is t2, relation of t1<t2 is satisfied. The widths and shapes of the first hole 50a and the second hole 50b are appropriately determined by those skilled in the art, without limit.

As described above, as a portion of the cathode electrode terminal 13T and the anode electrode terminal 12T are exposed outside toward the same direction with the height thereof being different from each other, it is easy to electrically connect an external connection terminal therewith. Further, thanks to this structure, in the X-ray emission apparatus to be described hereinafter, it is possible to align the direction of the X-ray source and secure electrical connection by simply mounting the cartridge-type X-ray source 600 to the cartridge mounting part.

In particular, that the cathode electrode terminal 13T and the anode electrode terminal 12T are exposed outside toward the same direction with the height thereof being different from each other is advantageous for improving insulating effect. In the embodiment, the anode electrode terminal 12T is exposed at a location higher than the cathode electrode terminal 13T, but not limited thereto; various changes may be made by those skilled in the art according to structures, such as locations and shapes, of the cathode electrode 13 and the anode electrode 12.

Figure 3:
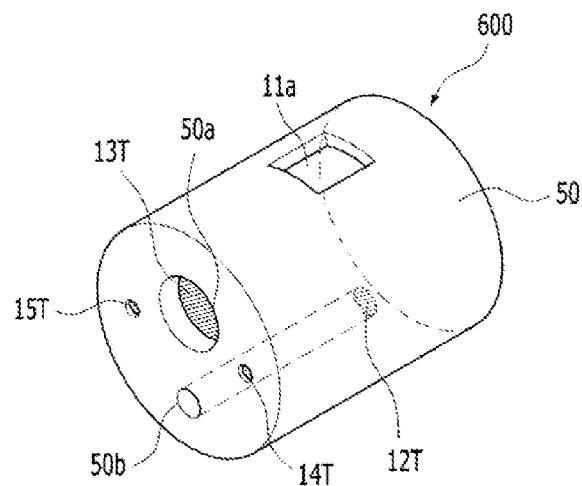
FIG. 3 is a bottom view showing the cartridge-type X-ray source of FIG. 2.

FIG. 3 is a bottom view showing the cartridge-type X-ray source of FIG. 2. Referring to FIG. 3, the above described cathode electrode terminal 13T is exposed through the first hole 50a that is formed on the bottom surface of the housing 50 of the cartridge-type X-ray source 600; and the above described anode electrode terminal 12T is exposed through second hole 50b that is formed to have a depth deeper than the first hole from the bottom surface of the housing 50.

The gate electrode terminal 14T connected to the above described gate electrode 14, and the focusing electrode terminal 15T connected to the above described focusing electrode 15 may be exposed through an additional through hole that is formed at a side of the cathode electrode terminal 13T on the bottom surface of the housing 50. However, without being limited thereto, the gate electrode terminal and the focusing electrode terminal may be exposed outside through the cathode electrode 13 in the same direction as the cathode electrode terminal 13T so as to be insulated from the cathode electrode 13.

Figure 4:
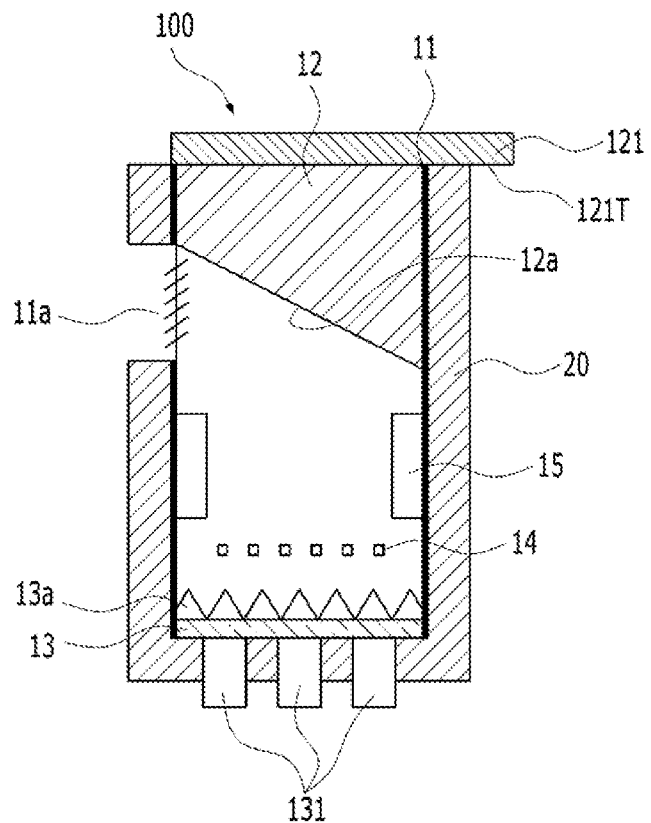
FIG. 4 is a schematic sectional view showing an X-ray source using a nanostructure according to an embodiment of the present invention.

FIG. 4 is a schematic sectional view showing an X-ray source using a nanostructure according to an embodiment of the present invention.

Referring to FIG. 4, compared with the X-ray source 10 according to the embodiment of FIG. 1, the X-ray source 100 according to the embodiment is configured such that an anode terminal electrode 121 is separately provided at the upper portion of the anode electrode 12, at least one protruding cathode terminal electrode 131 is separately provided at the lower portion of the cathode electrode 13, and the insulator 20 is disposed therebetween. Even in this case, the anode electrode terminal 121T, as a portion of the anode terminal electrode 121, and the cathode terminal electrode 131 are exposed outside toward the same direction with the height thereof being different from each other. Various changes in the shape of the cathode terminal electrode 131 may be made by those skilled in the art as long as the shape thereof allows the cathode terminal electrode to be electrically connected to the external connection terminal to be described hereinafter. Meanwhile, the cathode terminal electrode 131 may be integrally formed with the cathode electrode 13.

Figure 5:
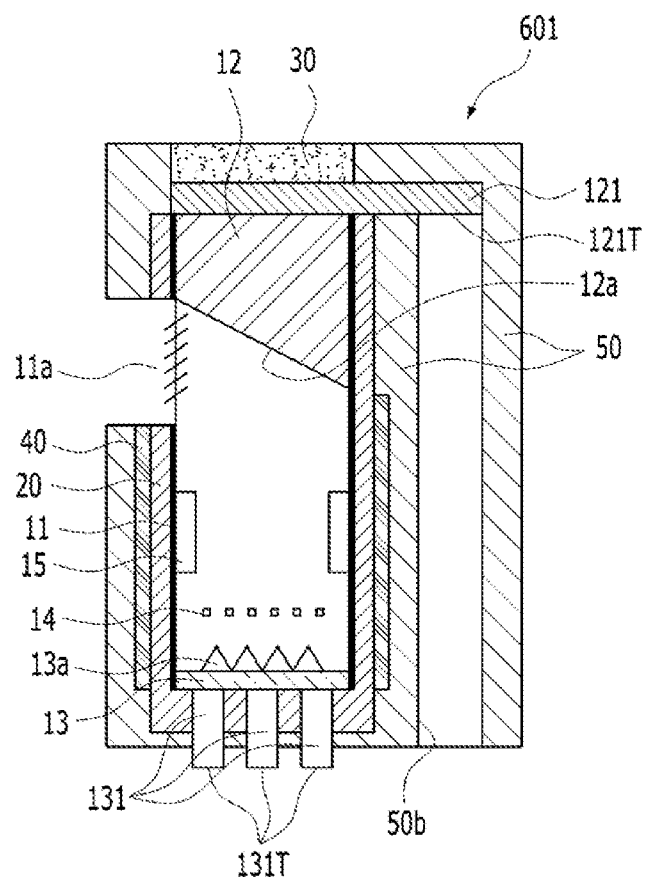
FIG. 5 is a schematic sectional view showing a cartridge-type X-ray source according to an embodiment of the present invention.

FIG. 5 is a schematic sectional view showing a cartridge-type X-ray source according to an embodiment of the present invention.

Referring to FIG. 5, compared with the X-ray source 100 according to the embodiment of FIG. 4, the X-ray source 601 according to the embodiment further includes the heat conductor 30, the shielding layer 40, and the housing 50 in addition to the X-ray source 100. Unlike the cartridge-type X-ray source 600 according to the embodiment of FIG. 2, the housing 50 is provided only with the second hole 50b on the bottom surface thereof for allowing the anode electrode terminal 121T to be exposed, the cathode electrode terminal 131T, as a portion of the at least one protruding cathode terminal electrode 131, is protrudingly exposed outside toward the same direction as the anode electrode terminal 121T.

The heat conductor 30 and the shielding layer 40 are the same as the description of the embodiment of FIG. 2. However, FIG. 5 is different from FIG. 2 in that the heat conductor 30 is exposed outside the housing 50 to improve heat dissipation efficiency, which may be similarly applied to the cartridge-type X-ray source 600 of FIG. 2.

Figure 6:
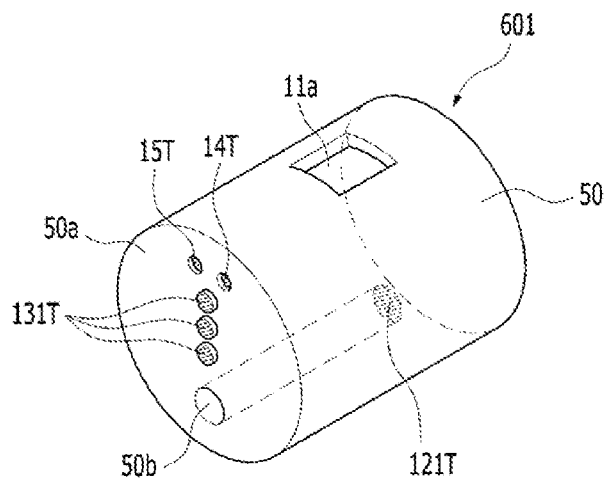
FIG. 6 is a bottom view showing the cartridge-type X-ray source of FIG. 5.

FIG. 6 is a bottom view showing the cartridge-type X-ray source of FIG. 5.

Referring to FIG. 6, a plurality of cathode electrode terminals 131T is exposed through the bottom surface of the housing 50 of the cartridge-type X-ray source 601; and the gate electrode terminal 14T and the focusing electrode terminal 15T are exposed around the cathode electrode terminals. Here, while not exposed outside, the gate electrode 14 and the focusing electrode 15 are insulated from the cathode electrode 13 and the cathode terminal electrode 131, respectively, and may be connected to the gate electrode terminal 14T and the focusing electrode terminal 15T through at least one of the cathode electrode and the cathode terminal electrode.

Figure 7:
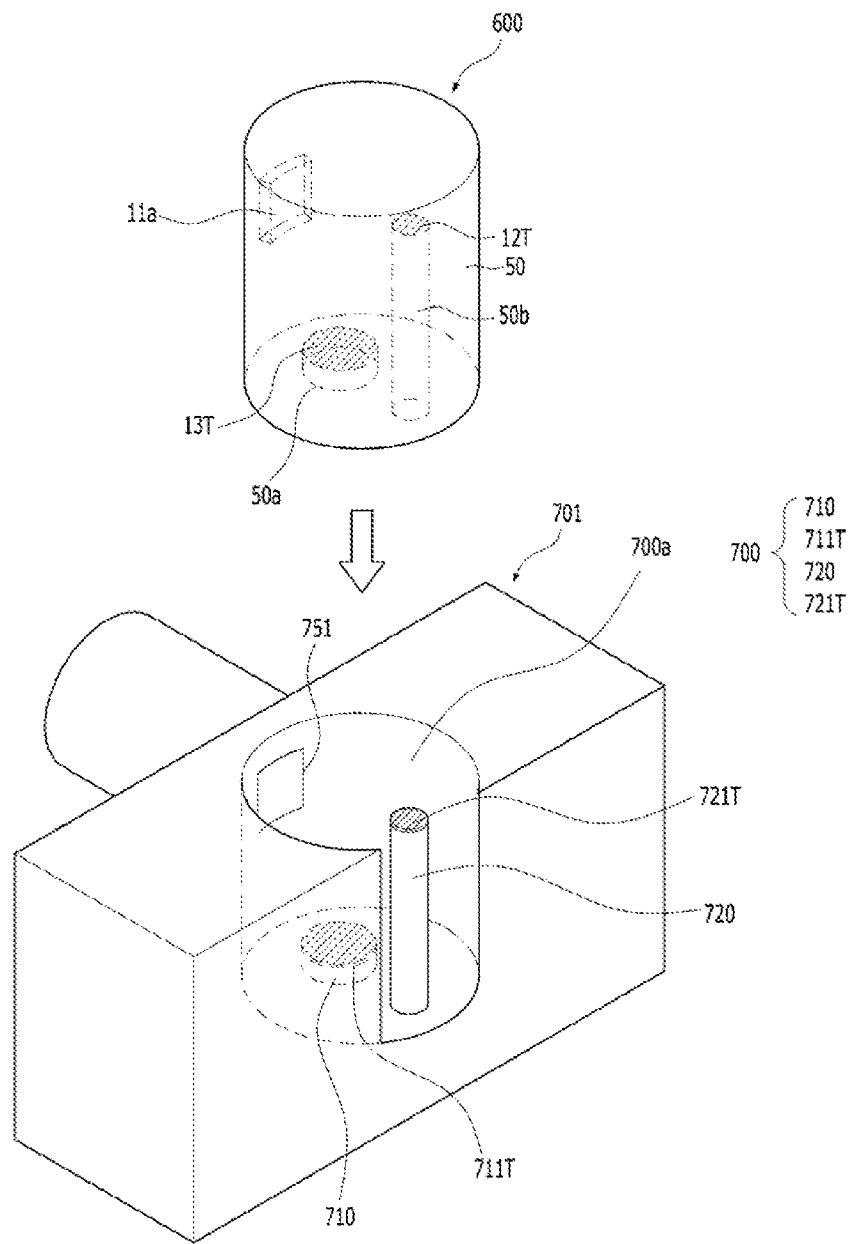
FIG. 7 is a schematic perspective view showing an X-ray emission apparatus using a cartridge-type X-ray source according to an embodiment of the present invention.

FIG. 7 is a schematic perspective view showing an X-ray emission apparatus using a cartridge-type X-ray source according to an embodiment of the present invention.

Referring to FIG. 7, a main body 701 of the X-ray emission apparatus according to the embodiment is configured such that the cartridge-type X-ray source 600 of FIG. 2 is mounted to the main body, and X-rays generated from the X-ray source are irradiated to a subject. Of course, instead of the cartridge-type X-ray source 600 of FIG. 2, another cartridge-type X-ray source, such as the cartridge-type X-ray source 601 of FIG. 5, may be mounted according to a configuration of the cartridge mounting part 700.

The X-ray emission apparatus according to the present invention includes the replaceable cartridge-type X-ray source 600 and the main body 701. The main body 701 includes the cartridge mounting part 700, which the cartridge-type X-ray source 600 is coupled with. The X-ray source 600 receives an input signal by electrical connection in a state where the X-ray source is mounted to the cartridge mounting part 700 of the main body 701, and emits X-rays generated by electric field emission, etc. through the window 11a. The main body 701 is provided with a corresponding part 751 corresponding to the window 11a so as to allow the emitted X-rays to be irradiated in a forward direction. Meanwhile, when the cartridge-type X-ray source 600 deteriorates as the life of the electron emission source constituted by a nanostructure comes to an end, it is possible to simply replace the cartridge with a new cartridge-type X-ray source 600.

The cartridge mounting part 700 of the main body 701 is provided with an accommodation space 700a for accommodating the cartridge-type X-ray source 600 therein. The inside of the accommodation space 700a is provided with a first connection structure 710 corresponding to the first hole 50a, and a second connection structure 720 corresponding to the second hole 50b. The upper portion of the first connection structure 710 may be provided with a first connection terminal 711T connected to the cathode electrode terminal 13T; and upper portion of the second connection structure 720 may be provided with a second connection terminal 721T connected to the anode electrode terminal 12T. Meanwhile, not shown in the drawings, the inside of the accommodation space 700a may be further provided with a third connection terminal and a fourth connection terminal respectively corresponding to the above described gate electrode terminal and the focusing electrode terminal.

Meanwhile, not shown in the drawings, the main body 701 may be provided with a predetermined circuit device therein. The predetermined circuit device serves to allow X-rays to be radiated to the outside by generating X-rays from the cartridge-type X-ray source 600 according to directions of a user. The predetermined circuit device may include: a power supply for supplying a driving voltage to connection terminals of the cartridge-type X-ray source 600, such as the cathode electrode terminal 13T, the anode electrode terminal 12T, and the like, using a battery or an outer power source; and a controller for allowing X-rays to be emitted according to directions of a user by controlling timing, time, an amount of current, or the like that apply the driving voltage directly to the cartridge-type X-ray source 600.

Figure 8:
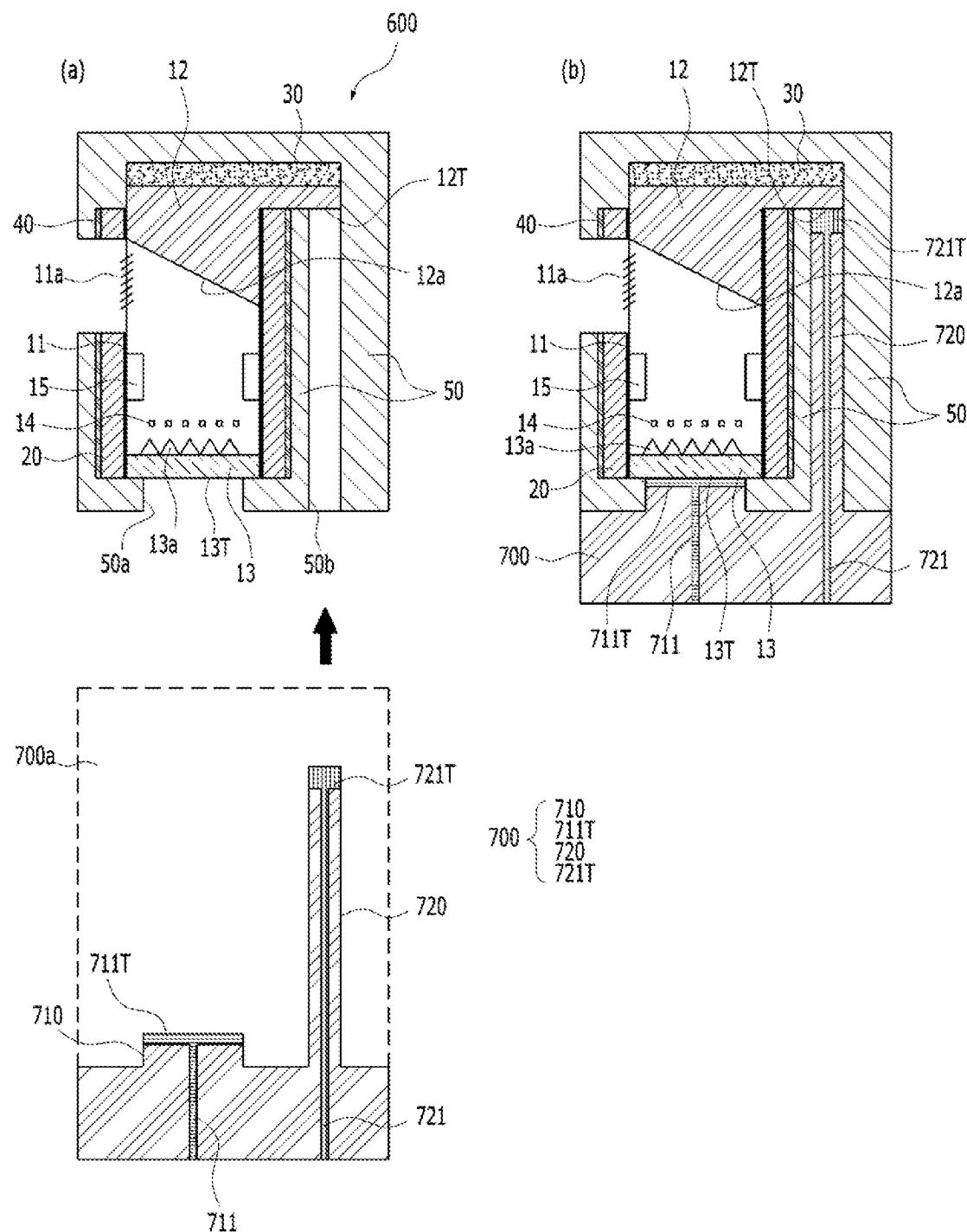
FIG. 8 includes a schematic sectional view (a) showing a state where the cartridge-type X-ray source of FIG. 2 is separated from a corresponding main body of an X-ray emission apparatus, and a schematic sectional view (b) showing a state where the cartridge-type X-ray source is engaged with the main body of the X-ray emission apparatus.

FIG. 8 includes a schematic sectional view (a) showing a state where the cartridge-type X-ray source of FIG. 2 is separated from a corresponding main body of an X-ray emission apparatus, and a schematic sectional view (b) showing a state where the cartridge-type X-ray source is engaged with the main body of the X-ray emission apparatus.

FIG. 8(a) shows the cartridge-type X-ray source 600 according to the embodiment of FIG. 2 and the cartridge mounting part 700, to which the cartridge-type X-ray source 600 is replaceably mounted in the main body of the X-ray emission apparatus. The configuration of the cartridge-type X-ray source 600 is the same as the description of FIG. 2.

The cartridge mounting part 700 of the main body of the X-ray emission apparatus includes: the first connection structure 710 provided with the first connection terminal 711T capable of being electrically connected to the cathode electrode 130; and the second connection structure 720 provided with the second connection terminal 721T, as an external electrode capable of being electrically connected to the anode electrode 120. Here, preferably, the first and the second connection structures 710 and 720 are respectively provided with the first connection terminal 711T and the second connection terminal 721T on the respective top surfaces thereof, and are in the form of column or protrusion facing the same direction while having different heights.

Further, it is preferred that the first connection structure 710 and the second connection structure 720 are provided apart from each other; and it is preferred that the first connection structure 710 and the second connection structure 720 have heights different from each other. In an embodiment of the present invention, the second connection structure 720 provided with the second connection terminal 721T has a height taller than that of the first connection structure 710 provided with the first connection terminal 711T, but is not limited thereto, and various changes may be made according to the cathode electrode 130 and the anode electrode 120 that are exposed outside toward the same direction with the height thereof being different from each other.

Further, if necessary, at least one of the first connection structure 710 and the second connection structure 720, and at least one of the first hole 50a and the second hole 50b of the X-ray source may be respectively provided with a locking protrusion and a locking groove, or the like to maintain a locking state.

Referring to FIG. 8(b), the X-ray source 600 is mechanically coupled with the cartridge mounting part 700 through the first connection structure 710 inserted into the first hole 50a and the second connection structure 720 inserted into the second hole 50b; and the cathode electrode terminal 130T is connected to the first connection terminal 711T and the anode electrode terminal 120T is connected to the second connection terminal 721T, and thereby the cartridge-type X-ray source 600 is electrically connected to the cartridge mounting part 700. Here, since the first connection structure 710 and the second connection structure 720 have different heights, it is easy to recognize the coupling direction of the cartridge-type X-ray source 600, and the direction is aligned by simply mounting. Further, in the first and the second connection structures 710 and 720, a first connection electrode 711 and a second connection electrode 721 that are provided for respectively connecting the first and the second connection terminals 711T and 721T to the predetermined circuit device in the main body are apart from each other the height thereof being different from each other, and thereby it is possible to improve insulating effect.

As described above, the cartridge-type X-ray source 600 is detachably coupled to the cartridge mounting part 700, accordingly it is possible to simply replace a new cartridge-type X-ray source when the life of the nanostructure constituting the electron emission source of the X-ray source comes to an end, and thus it is possible to improve economic efficiency.

Figure 9:
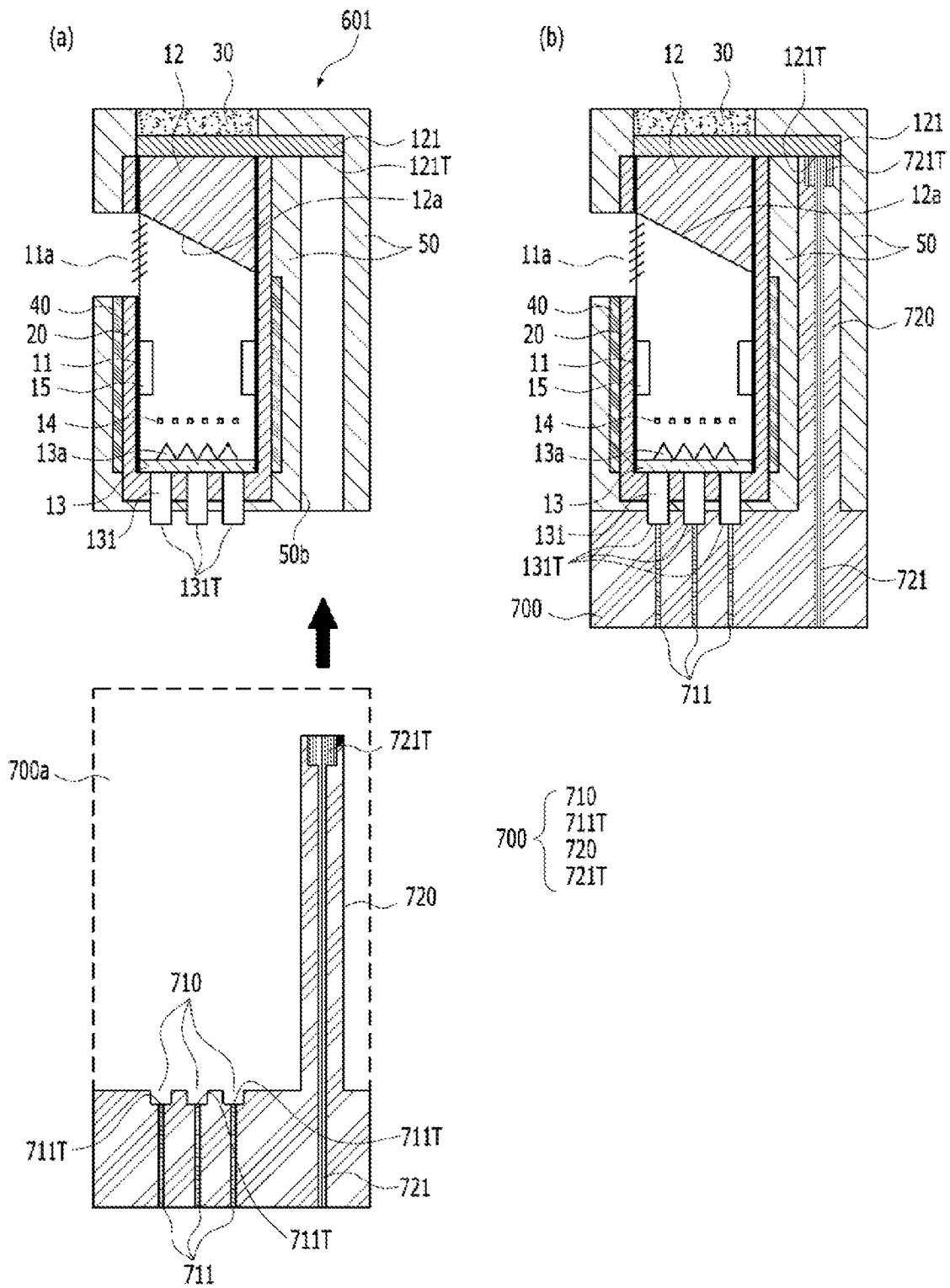
FIG. 9 includes a schematic sectional view (a) showing a state where the cartridge-type X-ray source of FIG. 5 is separated from a corresponding main body of an X-ray emission apparatus, and a schematic sectional view (b) showing a state where the cartridge-type X-ray source is engaged with the main body of the X-ray emission apparatus.

FIG. 9 includes a schematic sectional view (a) showing a state where the cartridge-type X-ray source of FIG. 5 is separated from a corresponding main body of an X-ray emission apparatus and a schematic sectional view (b) showing a state where the cartridge-type X-ray source is engaged with the main body of the X-ray emission apparatus.

Referring to views (a) and (b) of FIG. 9, the X-ray emission apparatus provided with the cartridge-type X-ray source 601 according to the embodiment of FIG. 5 is different from the embodiment of FIG. 8 in that the first connection structure 710 of the cartridge mounting part 700 has a concave shape. This is because the cathode electrode terminal 131T, which the first connection structure 710 is engaged with, has a convex shape.

As described above, the shape of the second connection structure 720 as well as the shape of the first connection structure 710 may be changed in various shapes according to shapes of the corresponding cathode electrode terminal 131T and the anode electrode terminal 121T or shapes of periphery parts.

Figure 10:
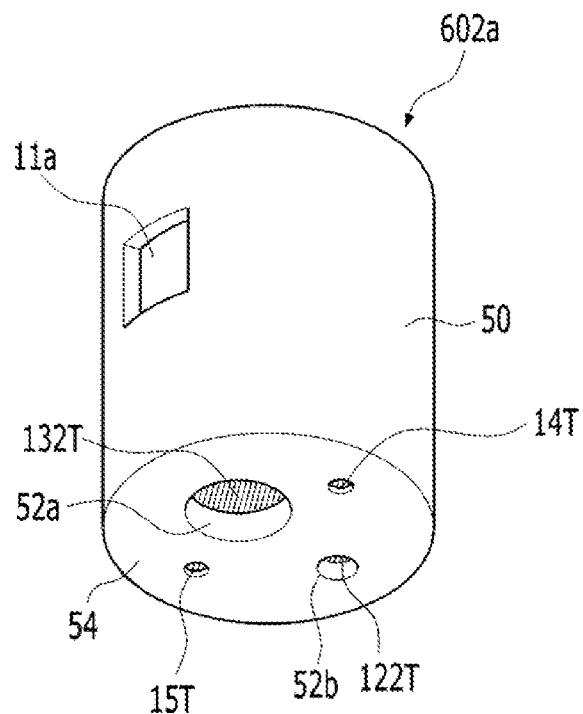
FIGS. 10 to 12 are views showing cartridge-type X-ray sources according to embodiments of the present invention.
Figure 11:
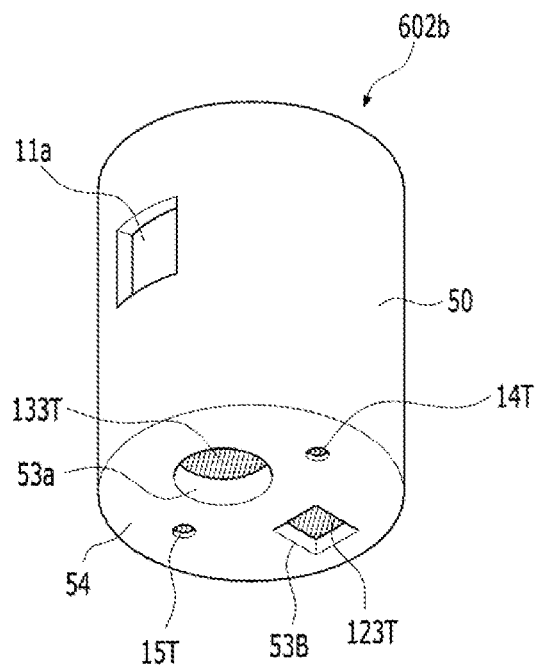
Figure 12:
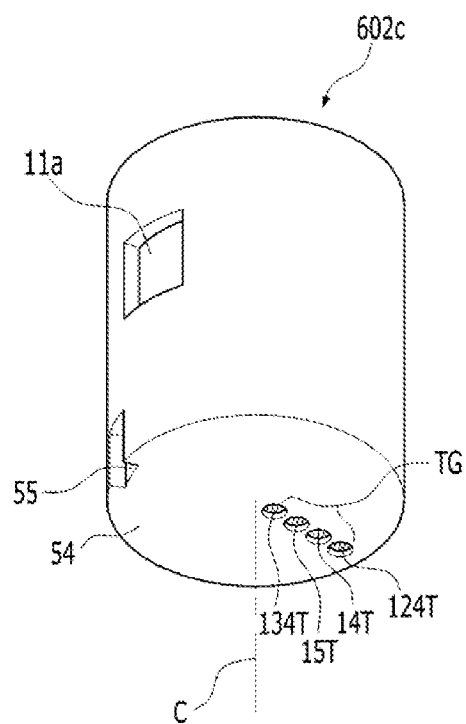

FIGS. 10 to 12 are views showing cartridge-type X-ray sources according to embodiments of the present invention.

The cartridge-type X-ray source 602 according to the embodiment is similar to or the same as the apparatus 600, 601 according to the embodiment of FIG. 2 or FIG. 5. in terms of the inner configuration. However, disposition, sizes, shapes, and the like of terminals exposed outside the housing 50 may be different from the embodiment of FIG. 2 or FIG. 5.

Referring to FIG. 10, the cartridge-type X-ray source 602a according to the embodiment may be provided on the bottom surface 54 of the housing 50 with a first hole 52a for allowing the cathode electrode terminal 132T to be exposed, and a second hole 52b for allowing the anode electrode terminal 122T to be exposed. The first hole 52a and the second hole 52b may be formed to have the same shape and depth, and have different sizes from each other.

Of course, the cartridge mounting part of the main body of the X-ray emission apparatus, which the cartridge-type X-ray source 602a is to be mounted to, is provided with first and second connection structures corresponding to the first hole 52a and the second hole 52b. Thanks to this configuration, when the cartridge-type X-ray source 602a is mounted to the main body of the X-ray emission apparatus, it is possible to secure alignment and stable electric connection of the apparatus by simply engaging each of the holes 52a and 52b with a corresponding connection structure. In particular, it is possible to fundamentally prevent making a mistake caused by confusing the cathode electrode terminal 132T with the anode electrode terminal 122T.

On the bottom surface 54 of the housing 50, the gate electrode terminal 14T and the focusing electrode terminal 15T that are mentioned in the above described embodiments may be exposed, and dispositions, shapes, and sizes thereof may not be limited to specific dispositions, shapes, and sizes, which is applied to embodiments with reference to FIGS. 11 and 12, hereinbelow.

Referring to FIG. 11, in the cartridge-type X-ray source 602b according to the embodiment, the bottom surface 54 of the housing 50 may be provided with a first hole 53a for allowing a cathode electrode terminal 133T to be exposed, and a second hole 53b a for allowing n anode electrode terminal 123T to be exposed. Herein, the first hole 53a and the second hole 53b may be formed to have the same depth, and to have shapes different from each other. For example, the first hole 53a and the cathode electrode terminal 133T may be formed to be in a circular shape; and the second hole 53b and the anode electrode terminal 123T may be formed to be in a quadrangular shape. Thanks to this configuration, when the cartridge-type X-ray source 602b is mounted to the main body of the X-ray emission apparatus, it is possible to secure alignment and stable electric connection of the apparatus by simply engaging each of the holes 53a and 53b with a corresponding connection structure.

Referring to FIG. 12, in the cartridge-type X-ray source 602c according to the embodiment, the bottom surface 54 of the housing 50 may be provided with an electrode terminal group TG including a cathode electrode terminal 134T and an anode electrode terminal 124T to be biased toward one direction based on the central axis C of the housing 50. Thanks to this configuration, when the cartridge-type X-ray source 602c is mounted to the main body of the X-ray emission apparatus, it is possible to secure alignment and stable electric connection of the apparatus by simply engaging the electrode terminal group TG with a corresponding connection terminal group including first and second connection terminals respectively corresponding to the cathode electrode terminal 134T and the anode electrode terminal 124T. Further, in order to secure more precise mount, a guide member 55 may be provided adjacent to the bottom surface of the housing 50 for guiding a coupling direction when mounting.

Figure 13:
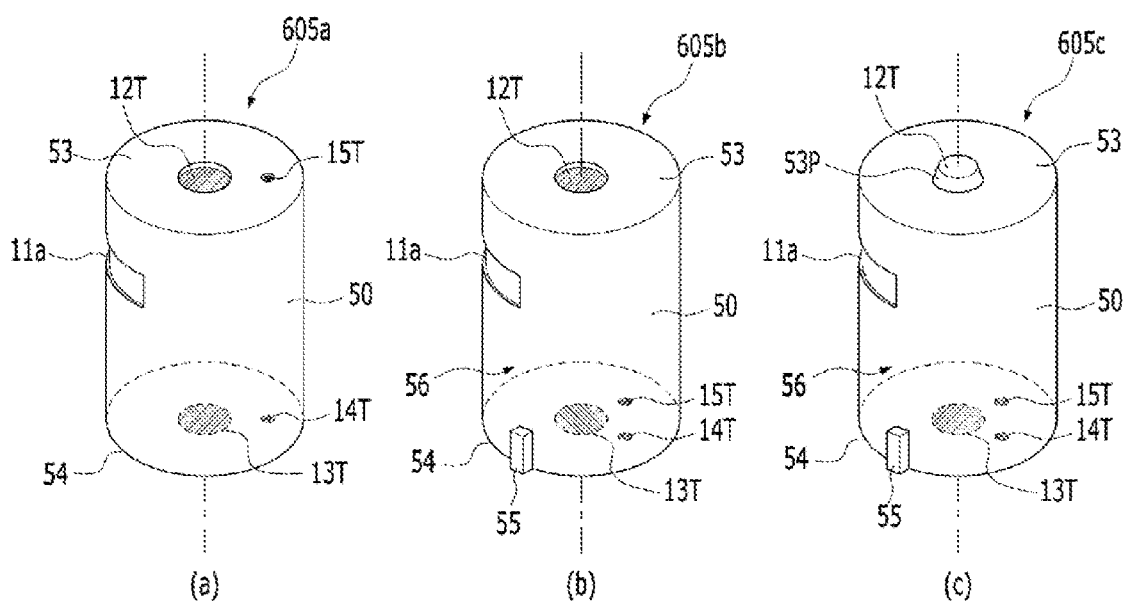
FIG. 13 are views showing a cartridge-type X-ray source according to an embodiment of the present invention.

FIG. 13 shows a cartridge-type X-ray source according to an embodiment of the present invention.

The cartridge-type X-ray source 605a, 605b, 605c according to the embodiment is similar to or the same as the apparatus 600, 601 according to the embodiment of FIG. 2 or FIG. 5. in terms of the inner configuration. However, disposition, sizes, shapes, and the like of terminals exposed outside the housing 50 may be different from the embodiment of FIG. 2 or FIG. 5.

In the cartridge-type X-ray source 605a, 605b, 605c according to the embodiment, the housing 50 may be constituted by a plurality of surfaces that form the appearance thereof; and the anode electrode terminal 12T and the cathode electrode terminal 13T may be respectively exposed to the outside through different surfaces of the plurality of surfaces. The housing 50 may be in a cylindrical shape having an upper surface 53, a bottom surface 54, and a side surface 56. In this case, the anode electrode terminal 12T and the cathode electrode terminal 13T may be exposed to the outside respectively through the upper surface 53 and the bottom surface 54.

Firstly, referring to a view (a) of FIG. 13, in the cartridge-type X-ray source 605a, the anode electrode terminal 12T is exposed through the upper surface 53 of the housing 50. Referring to the inner configuration shown in FIGS. 2 and 5, since the anode electrode is disposed at the upper portion in the X-ray source 605a, that the terminal electrode, which is a portion of or connected to the anode electrode, is exposed through the upper surface 53, is advantageous for shortening a transfer path for a high-voltage electric signal. Meanwhile, the cathode electrode terminal 13T may be exposed through the bottom surface 54 of the housing 50, which is opposite to the anode electrode terminal 12T. Here, the gate electrode terminal 14T electrically connected the gate electrode, and the focusing electrode terminal 15T electrically connected the focusing electrode may be provided respectively on the upper surface 53 and the bottom surface 54. The disposition of the gate electrode terminal and the focusing electrode terminal shown in the view (a) of FIG. 13 may be reversed.

In the case where the cartridge-type X-ray source 605a is mounted to the main body of the X-ray emission apparatus, when the cartridge-type X-ray source is mounted by distinguishing the upper surface 53 and the bottom surface 54 based on the location of the window 11a, it is possible to align the direction of the window 11a by contacting the gate electrode terminal 14T and the focusing electrode terminal 15T with respective corresponding connection terminals.

Next, referring to a view (b) of FIG. 13, in the cartridge-type X-ray source 605b, both of the above described gate electrode terminal 14T and focusing electrode terminal 15T may be exposed through the bottom surface 54 of the housing 50. Meanwhile, the cylindrical-shaped housing 50 may be provided with the guide member 55 on the side surface 56 thereof so as to guide the coupling direction by protruding from the surface.

Of course, the guide member 55 shown in this figure and the rest figures may be formed in a convex shape or in a concave shape. In the case where the guide member 55 is provided, it is natural that the cartridge mounting part of the main body of the X-ray emission apparatus should be provided with a corresponding part.

Next, referring to a view (b) of FIG. 13, in the cartridge-type X-ray source 605c, anode electrode terminal 12T exposed through the upper surface 53 includes a protrusion 53p protruding from the upper surface 53. The configuration of the rest electrode terminals 13T, 14T, and 15T, and guide member 55 is the same as the above description of the X-ray source 605b in the view (b) of FIG. 13. Through this configuration, it is possible to easily distinguish the upper surface 53 and the bottom surface 54.

Figure 14:
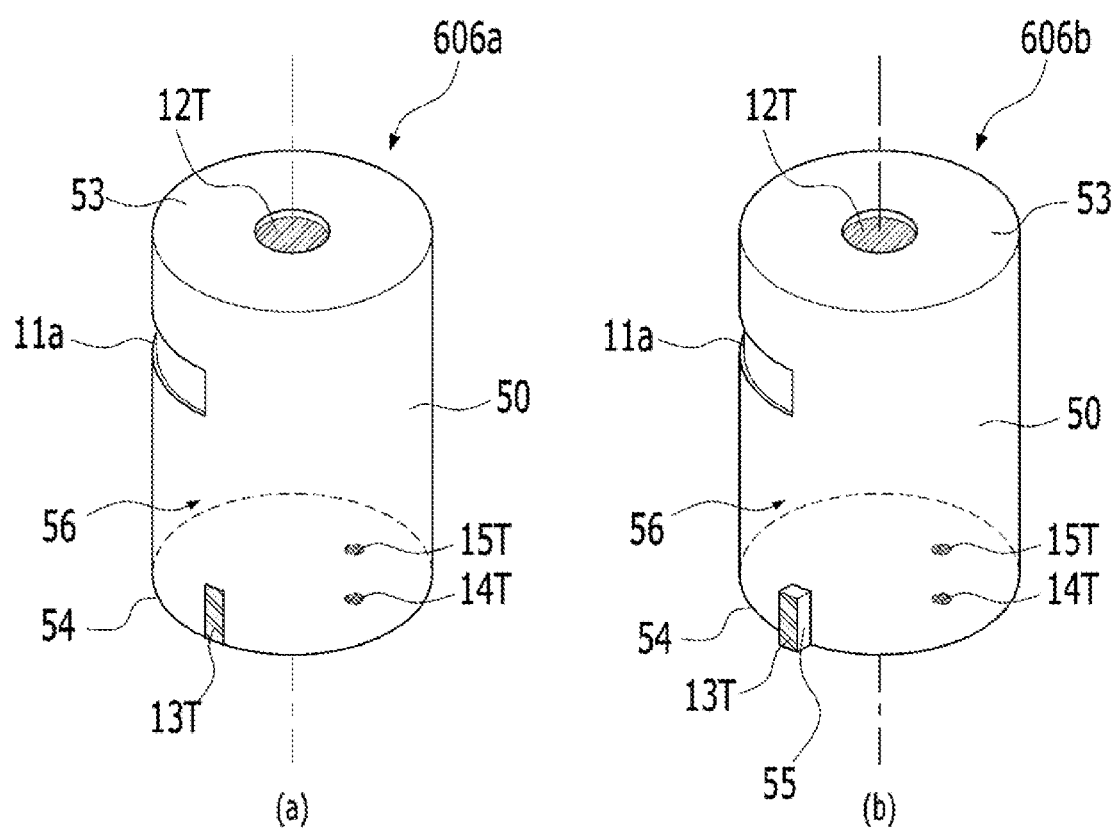
FIG. 14 are views showing a cartridge-type X-ray source according to an embodiment of the present invention.

FIG. 14 shows a cartridge-type X-ray source according to an embodiment of the present invention.

In the cartridge-type X-ray source 606a, 606b according to the embodiment, the housing 50 forms a cylindrical appearance. Either the anode electrode terminal 12T or the cathode electrode terminal 13T is exposed through one surface selected from between the upper surface and the bottom surface, and the other is exposed to the outside through the side surface, which has a direction crossing the directions of the upper surface and the bottom surface. For example, the anode electrode terminal 12T may be exposed through the upper surface 53 of the housing 50, and cathode electrode terminal 13T may be exposed to the outside through the side surface 56 of the housing 50. Meanwhile, On the bottom surface 54 of the housing 50, the gate electrode terminal 14T and the focusing electrode terminal 15T that are mentioned in the above described embodiments may be exposed, and dispositions, shapes, and sizes thereof may not be limited to specific dispositions, shapes, and sizes, which are applied to embodiments with reference to FIGS. 11 and 12, hereinbelow.

Referring to a view (a) of FIG. 14, the cathode electrode terminal 13T is exposed through the side surface 56 of the cylindrical housing 50. When the cartridge-type X-ray source 606a is mounted to the cartridge mounting part of the main body, it is possible to align the direction of the window 11a and possible to secure electrical connection of the gate electrode terminal 14T and the focusing electrode terminal 15T by simply matching the direction of the cathode electrode terminal 13T.

Referring to a view (b) of FIG. 14, the side surface 56 may be provided with the above described guide member 55; and the cathode electrode terminal 13T is provided at a portion of the guide member 55. In this case, the guide member 55 serves to guide the coupling direction of the cartridge, and to secure electrical connection, simultaneously.

Figure 15:
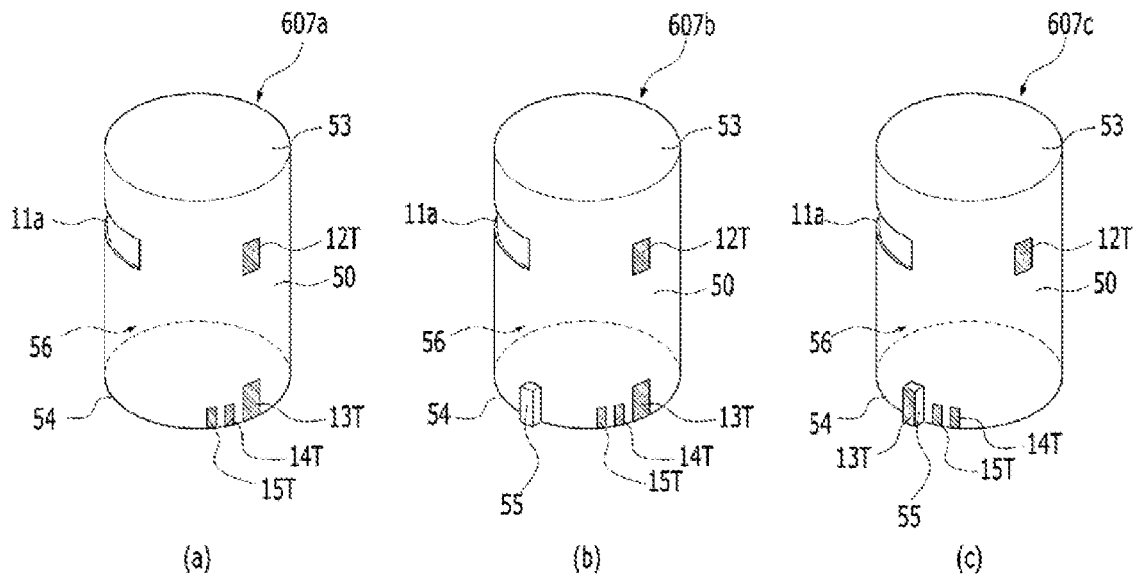
FIG. 15 are views showing a cartridge-type X-ray source according to an embodiment of the present invention.

FIG. 15 shows a cartridge-type X-ray source according to an embodiment of the present invention.

FIG. 15 shows examples where the anode electrode terminal 12T and the cathode electrode terminal 13T are exposed through the side surface 56 of the cylindrical housing 50 in the X-ray source 607a, 607b, 607c.

Referring to a view (a) of FIG. 15, the anode electrode terminal 12T and the cathode electrode terminal 13T may be exposed respectively through the upper portion and the lower portion of the side surface 56 of the housing 50 in the X-ray source 607a according to the embodiment. Here, the gate electrode terminal 14T and the focusing electrode terminal 15T may also be exposed through the side surface 56, and may not be limited to specific locations. However, that the gate electrode terminal and the focusing electrode terminal are disposed close to the cathode electrode terminal 13T over the anode electrode terminal 12T is advantageous in terms of inner configuration and electrical insulation.

Referring to a view (b) of FIG. 15, the side surface 56 may be further provided with the above described guide member 55 with reference to the view (b) of FIG. 13. Further, referring to a view (c) of FIG. 15, as the above description with reference to the view (b) of FIG. 14, the cathode electrode terminal 13T may be disposed on the guide member 55. Further, the anode electrode terminal 12T and the cathode electrode terminal 13T may be exposed toward different directions based on the central axis of the cylindrical housing 50.

Figure 16:
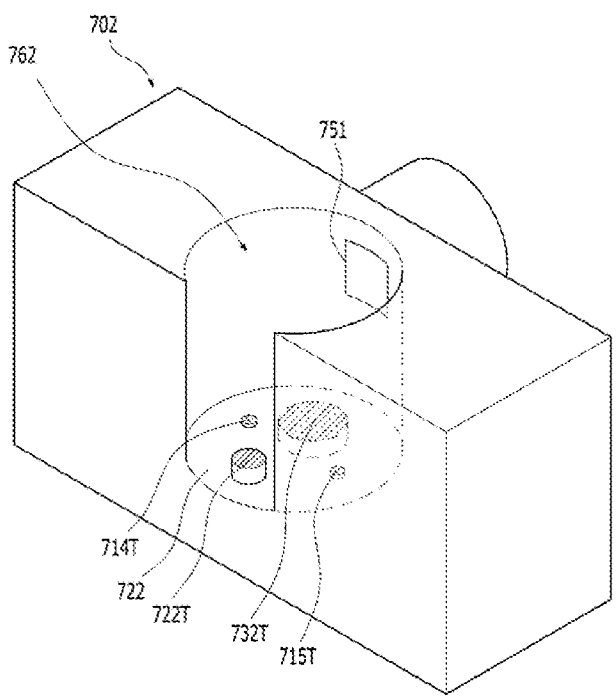
FIG. 16 is a view showing an embodiment of a main body of an X-ray emission apparatus compatible with the cartridge-type X-ray source of FIG. 10.

FIG. 16 is a view showing an embodiment of a main body of an X-ray emission apparatus compatible with the cartridge-type X-ray source of FIG. 10.

A main body 702 of the X-ray emission apparatus according to the embodiment is provided with a cartridge mounting part 762, to which the cartridge-type X-ray source 602a according to the embodiment of FIG. 10 is mounted. As in the above description with reference to FIG. 7, the X-ray source 602a receives an input signal by being electrically connected to a predetermined circuit device in the main body in a state where the X-ray source is mounted to the cartridge mounting part 702 of the main body 701, and emits X-rays generated by electric field emission, etc. through the window. The main body 702 is provided with a corresponding part 751 corresponding to the window such that the X-rays are emitted in a forward direction.

For reference, the predetermined circuit device in the main body serves to allow X-rays to be radiated to the outside by generating X-rays from the cartridge-type X-ray source 602a according to directions of a user. The predetermined circuit device may include: a power supply for supplying a driving voltage to anode, cathode, gate, and focusing electrodes of the cartridge-type X-ray source 602a, using a battery or an outer power source; and a controller for allowing X-rays to be generated according to directions of a user by controlling timing, time, an amount of current, or the like that apply the driving voltage directly to the cartridge-type X-ray source 602a.

The cartridge mounting part 762 of the main body 702 is provided with a first connection terminal 732T and a second connection terminal 722T on the bottom surface thereof 772. The first and the second connection terminals 732T and 722T respectively correspond to the cathode electrode terminal 132T and the anode electrode terminal 122T of FIG. 10. In other words, the first and the second connection terminals are provided and disposed to be respectively electrically connected to corresponding electrode terminals, which correspond to the first and the second connection terminals with the height and the direction thereof being the same, relative to the X-ray source 602a. Further, the bottom surface 772 may be provided with a third connection terminal 714T and a fourth connection terminal 715T so as to respectively correspond to the gate electrode terminal and the focusing electrode terminal of the X-ray source.

Figure 17:
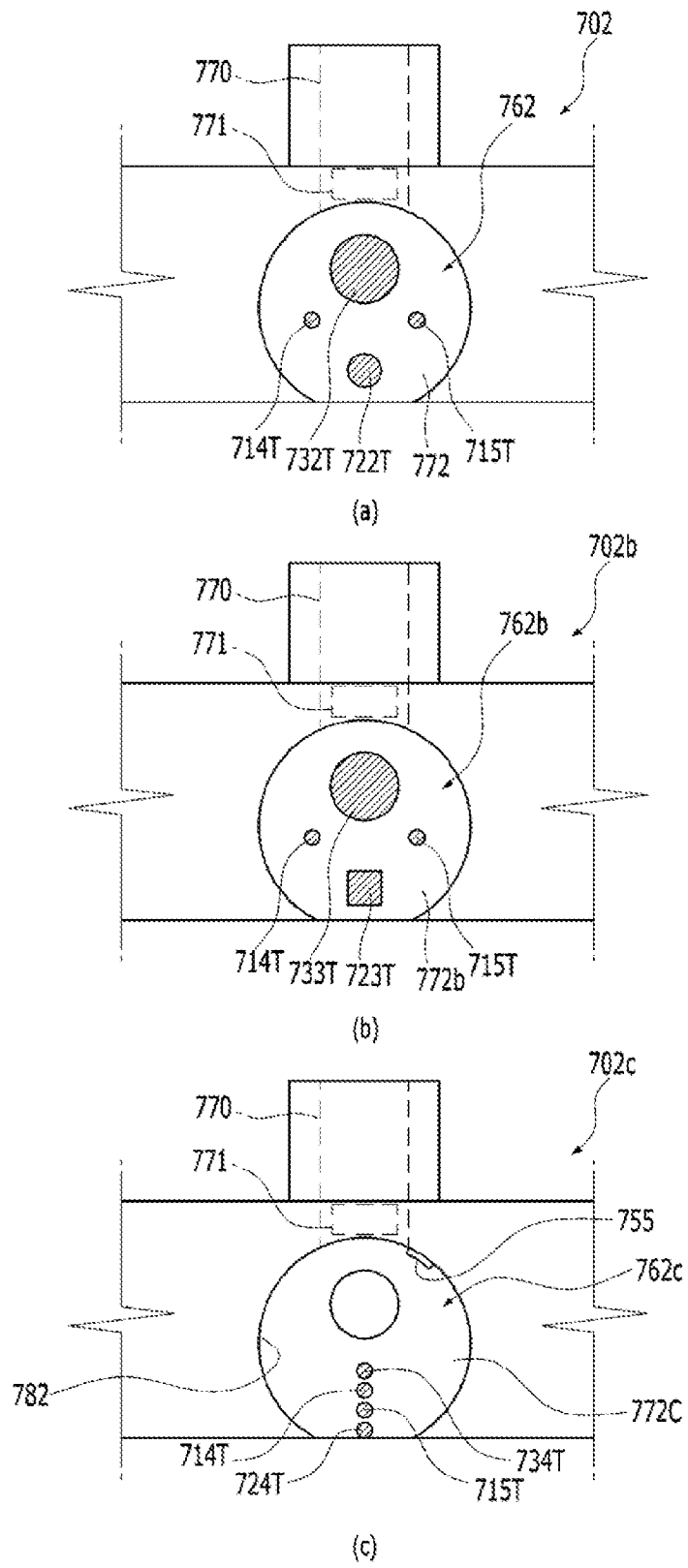
FIG. 17 are views showing various examples of a cartridge mounting part in the main body of the X-ray emission apparatus according to the embodiment of FIG. 16.

FIG. 17 shows various examples of a cartridge mounting part in the main body of the X-ray emission apparatus according to the embodiment of FIG. 16.

Firstly, a view (a) of FIG. 17 shows the cartridge mounting part 762 of the main body 702 of the X-ray emission apparatus shown in FIG. 16, wherein on the bottom surface 772, the first connection terminal 732T is disposed at a location close to the X-ray irradiation path 770, and the second connection terminal 722T is disposed at a location opposite to the X-ray irradiation path. The first connection terminal 732T is in the same circular shape as the second connection terminal, but the flat surface thereof is bigger than that of the second connection terminal, and thereby it is possible to easily distinguish the first connection terminal and the second connection terminal 722T. Meanwhile, the first connection terminal 732T and the second connection terminal 722T may be formed to protrude from the bottom surface 772, wherein the first connection terminal and the second connection terminal may include first and second connection structures correspondingly protruding to respective sizes of the first and the second holes 52a and 52b formed in the cartridge-type X-ray source 602a of FIG. 10. The third connection terminal 714T and the fourth connection terminal 715T are the same as the description of FIG. 16.

Meanwhile, the main body 702 of the X-ray emission apparatus may be provided with a collimator 771 on the X-ray irradiation path 770. The collimator 771 may control an irradiation range of the X-rays emitted through the window of the X-ray source.

Referring to a view (b) of FIG. 17, a main body 702b according to the embodiment may include a first connection terminal 733T and a second connection terminal 723T, which have different shapes from each other, provided on a bottom surface 772b of a cartridge mounting part 762b. For example, the first connection terminal 733T may be formed to be in a circular shape; and the second connection terminal 723T may be formed to be in a quadrangular shape, but not limited thereto, which corresponds to the X-ray source 602b shown in the view (b) of FIG. 10. Accordingly, the first connection terminal and the second connection terminal may be formed in any shapes as long as the shapes thereof correspond to shapes of the cathode electrode terminal and the anode electrode terminal on the bottom surface of the X-ray source. The bottom surface 772b may be provided with a third connection terminal 714T and a fourth connection terminal 715T so as to respectively correspond to the gate electrode terminal and the focusing electrode terminal of the X-ray source.

Referring to a view (c) of FIG. 17, a main body 702c according to the embodiment may include a first connection terminal 734T and a second connection terminal 724T having the same shape and size provided on a bottom surface 772c of a cartridge mounting part 762c. The first and the second connection terminals may have the same shape and size as third and fourth connection terminals 714T and 715T. The first to the fourth connection terminals 734T, 724T, 714T, and 715T may be disposed to be biased toward one direction based on the center of the bottom surface 772c so as to correspond to the electrode terminal group TG of the X-ray source 602c of FIG. 12. For example, the first to the fourth connection terminals may be disposed to be biased to a location opposite to the X-ray irradiation path 770. Further, at a portion of a side wall 782 of the cartridge mounting part 762c, a guide member 755 may be provided adjacent to the bottom surface 772c for guiding a coupling direction when the cartridge-type X-ray source is mounted thereto in order to allow a more precise mount. The guide member 755 is formed to be engaged with the guide member 55 of the X-ray source 602*c*.

Figure 18:
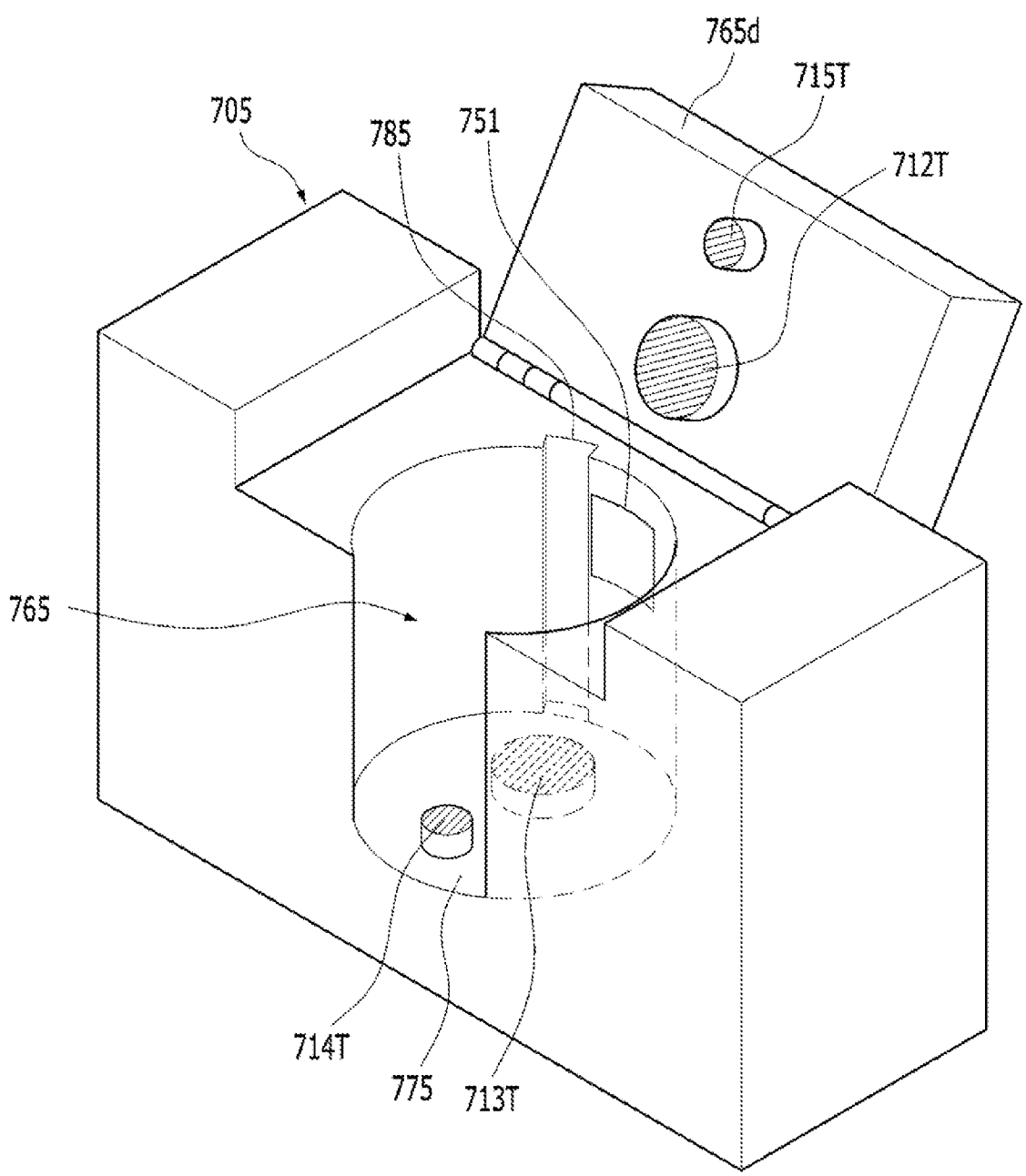
FIG. 18 is a view showing an embodiment of a main body of an X-ray emission apparatus compatible with the cartridge-type X-ray source of FIG. 13(*a*)

FIG. 18 is a view showing an embodiment of a main body of an X-ray emission apparatus compatible with the cartridge-type X-ray source in the view (b) of FIG. 13.

Referring to FIG. 18 and the view (a) of FIG. 13, a main body 705 of the X-ray emission apparatus according to the embodiment is provided with a cartridge mounting part 765 having an accommodation space for the cartridge-type X-ray source 605*a* in the view (a) of FIG. 13. The cartridge mounting part 765 may be provided with a cover 765*d* at the upper portion thereof for covering the top surface thereof. The cover 765*d* may be hinged to the main body 705 to be opened and closed. In this case, the bottom surface 775 of the cartridge mounting part 765 may be provided with a first connection terminal 713T and a third connection terminal 714T corresponding to the cathode electrode terminal and the gate electrode terminal provided on the bottom surface of the X-ray source 605*a*; and the cover 765*d* may be provided with a second connection terminal 712T and a fourth connection terminal 715T corresponding to the anode electrode terminal and the focusing electrode terminal provided on the upper surface of the X-ray source 605*a*. The arrangement of the connection terminals may vary depending on how the electrode terminals are disposed on the upper surface and the bottom surface of the X-ray source 605*a*.

Meanwhile, as shown in the view (b) or (c) of FIG. 13, for compatibility with the X-ray source 605*b*, 605*c* having the guide member 55, the cartridge mounting part 765 may include a guide member 785 provided on a side wall thereof for guiding a coupling direction. The guide member 785, for example, may be formed in a groove shape.

Figure 19:
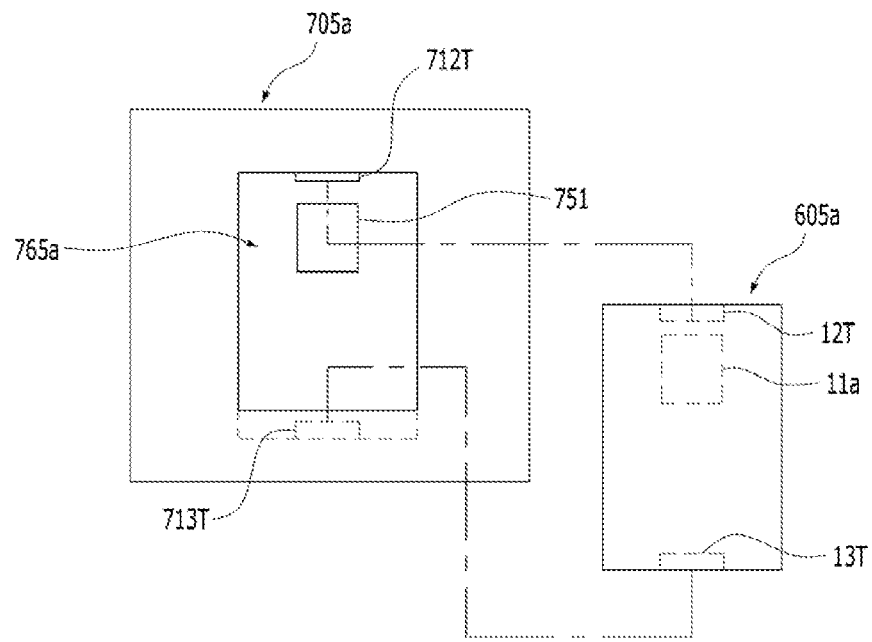
FIG. 19 is a view showing another embodiment of a main body of an X-ray emission apparatus compatible with the cartridge-type X-ray source of FIG. 13(*a*)

FIG. 19 is a view showing another embodiment of a main body of an X-ray emission apparatus compatible with the cartridge-type X-ray source in the view (a) of FIG. 13.

Referring to FIG. 19 and the view (a) of FIG. 13, a main body 705*a* of the X-ray emission apparatus according to the embodiment may include a grooved cartridge mounting part 765*a* on a rear surface thereof, that is, at a location opposite to the X-ray irradiation path. The cartridge mounting part 765*a*, for example, may allow the X-ray source 605*a* shown in the view (a) of FIG. 13 to be mounted thereto. The X-ray source 605*a* is provided with the anode electrode terminal 12T and the cathode electrode terminal 13T respectively on the upper surface and the bottom surface thereof, and in order to correspond to the anode electrode terminal and the cathode electrode terminal, the cartridge mounting part 765*a* is also provided with a second connection terminal 712T and a first connection terminal 713T respectively at the upper portion and the lower portion thereof. Further, the cartridge mounting part 765*a* is provided with a corresponding part 751 to correspond to the window 11*a* of the X-ray source 605*a*. Not shown in the drawings, the cartridge mounting part 765*a* is also provided with third and fourth connection terminals corresponding to the gate electrode terminal and the focusing electrode terminal.

Figure 20:
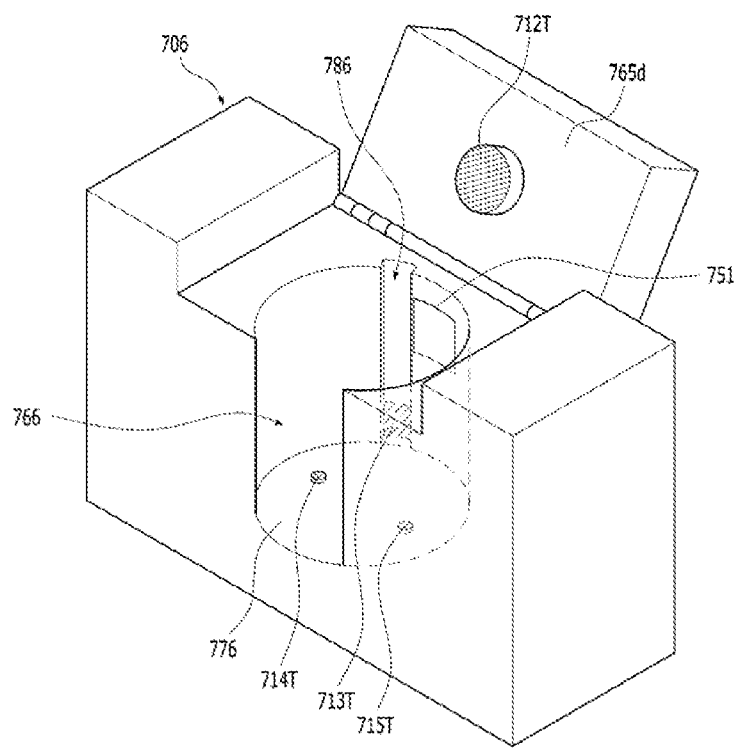
FIG. 20 is a view showing an embodiment of a main body of an X-ray emission apparatus compatible with the cartridge-type X-ray source of FIG. 14(*b*)

FIG. 20 is a view showing an embodiment of a main body of an X-ray emission apparatus compatible with the cartridge-type X-ray source in the view (b) of FIG. 14.

Referring to FIG. 20 and the view (b) of FIG. 14, a main body 706 of the X-ray emission apparatus according to the embodiment is provided with a cartridge mounting part 766 having an accommodation space for the cartridge-type X-ray source 606*b* the view (b) of FIG. 14. The cartridge mounting part 766 may be provided with the cover 765*d*, which is similar to the embodiment of FIG. 18, at the upper portion thereof for covering the top surface thereof. The cover 765*d* may be also hinged to the main body 706 to be opened and closed.

The cartridge mounting part 766 may be with a guide member 786 on a side wall thereof for guiding a coupling direction by being engaged with the guide member 55 of the cartridge-type X-ray source 606*b*. The guide member 786, for example, may be formed in a groove shape. Further, the cartridge mounting part 766 may be provided a first connection terminal 713T at a lower portion of the guide member 786 so as to correspond to the cathode electrode terminal 13T. The cartridge mounting part 766 may be provided on the bottom surface 776 thereof with a third connection terminal 714T and a fourth connection terminal 715T corresponding to the gate electrode terminal 14T and the focusing electrode terminal 15T provided on the bottom surface of the X-ray source 606*b*; and the cover 765*d* may be provided thereinside with a second connection terminal 712T corresponding to the anode electrode terminal 12T provided on the upper surface of the X-ray source 606*b*. The arrangement of the connection terminals may vary depending on how the electrode terminals are disposed on the upper surface, the bottom surface, and the side surface of the X-ray source 606*b*.

Figure 21:
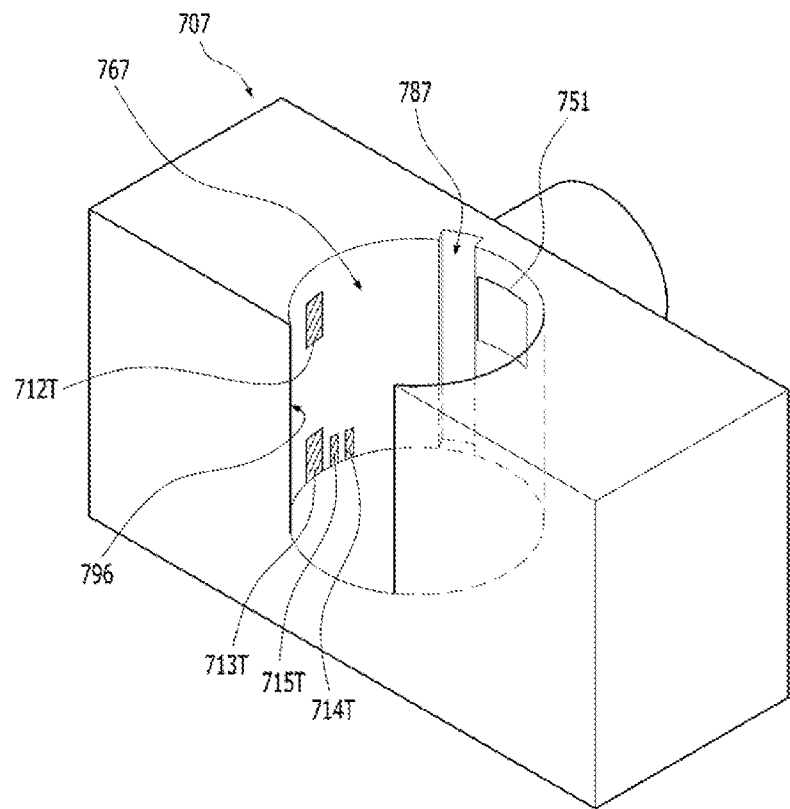
FIG. 21 is a view showing an embodiment of a main body of an X-ray emission apparatus compatible with the cartridge-type X-ray source of FIG. 15(*b*)

FIG. 21 is a view showing an embodiment of a main body of an X-ray emission apparatus compatible with the cartridge-type X-ray source of in the view (b) of FIG. 15.

Referring to FIG. 21 and the view (b) of FIG. 15, a main body 707 of the X-ray emission apparatus according to the embodiment is provided with a cartridge mounting part 767 having an accommodation space for the cartridge-type X-ray source 607*b* in the view (b) of FIG. 15. The upper portion of the cartridge mounting part 767 may be open, and the side surface 796 of the cartridge mounting part may be provided with a guide member 787, similar to the embodiment of FIG. 18 or 20. Further, the side surface 796 may be provided with a first connection terminal 713T and a second connection terminal 712T respectively corresponding to the cathode electrode terminal 13T and the anode electrode terminal 12T, and may be provided with third and fourth connection terminals 714T and 715T corresponding to the gate electrode terminal 14T and the focusing electrode terminal 15T. Of course, the arrangement of the connection terminals may vary depending on arrangement of the electrode terminals of the X-ray source 607*b*.

Figure 22:
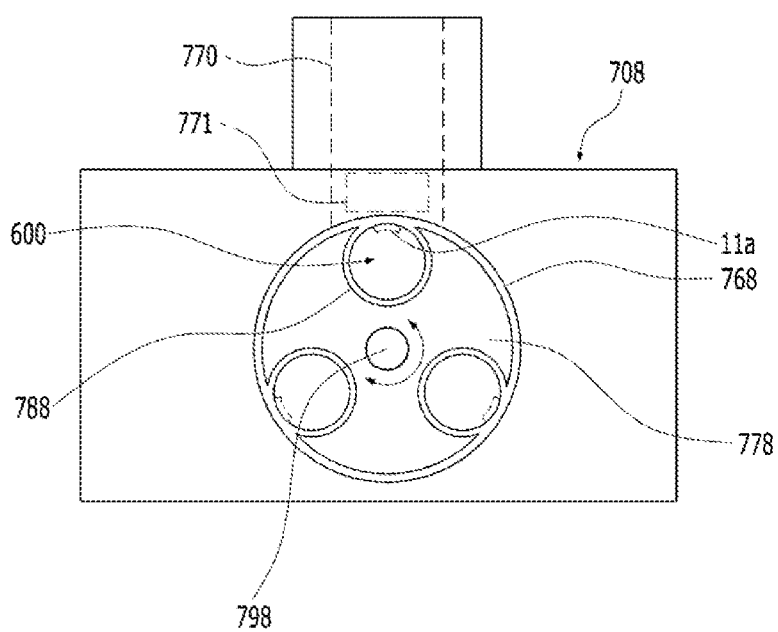
FIG. 22 is a view showing an embodiment of an X-ray emission apparatus, to which a plurality of cartridge-type X-ray sources is mounted.

FIG. 22 is a view showing an embodiment of an X-ray emission apparatus, to which a plurality of cartridge-type X-ray sources is mounted.

The X-ray emission apparatus 708 according to the embodiment may be configured such that a plurality of cartridge-type X-ray sources 600 is mounted thereto. To achieve this, the X-ray emission apparatus 708 may include, for example, a rotary loader 778, to which a plurality of cartridge-type X-ray sources 600 is mounted in a manner similar to how bullets are loaded into a revolver. The rotary loader 778 is provided with the cartridge mounting part 788 in plural, and rotates about a rotation axis 798 within a cylindrical space 768.

The rotary loader 778 may be configured to be temporarily locked until a user intentionally rotates the rotary loader when one selected window 11*a* of a cartridge-type X-ray source 600 is aligned with the X-ray irradiation path 770. The X-ray irradiation path 770 may be provided with the collimator 771 for controlling an irradiation range of X-rays. Thereby, it is possible to immediately replace with a new X-ray source by rotating the rotary loader 778 when a problem occurs in the X-ray source 600 being used.

Herein, an external appearance and an arrangement of the electrode terminals of the X-ray source 600, and shapes of the accommodation space and an arrangement of the connection terminals of the cartridge mounting part 788 may be changed variously including the above described embodiments.

Figure 23:
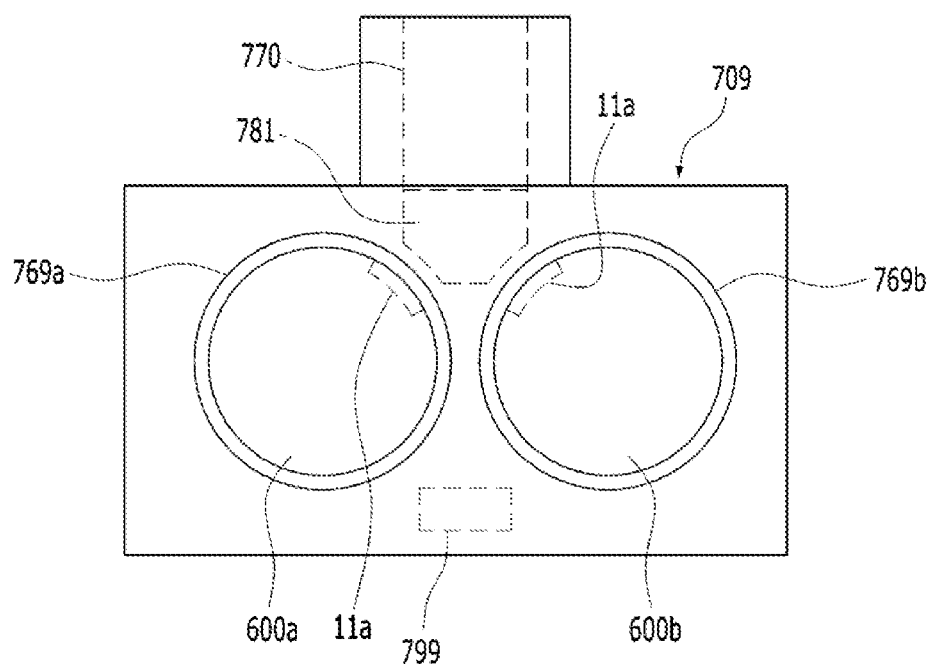
FIG. 23 is a view showing an embodiment of an X-ray emission apparatus, to which a plurality of cartridge-type X-ray sources is mounted.

FIG. 23 is a view showing an embodiment of an X-ray emission apparatus, to which a plurality of cartridge-type X-ray sources is mounted.

The X-ray emission apparatus 709 according to the embodiment may allow a plurality of, for example, two cartridge-type X-ray sources 600a and 600b to be mounted thereto simultaneously. To achieve this, the X-ray emission apparatus is provided with a number of cartridge mounting parts 769a and 769b equal to the number of the cartridge-type X-ray sources to be simultaneously mounted thereto. The two X-ray sources 600a and 600b are mounted such that windows 11a thereof face the X-ray irradiation path 770, wherein a multi-collimator 781 may be provided in the X-ray irradiation path 770. The multi-collimator 781 controls X-rays emitted from at least one of the two X-ray sources 600a and 600b to be irradiated within a predetermined irradiation range through the X-ray irradiation path 770.

Meanwhile, the X-ray emission apparatus 709 may be further provided with a controller 799 controlling selectively driving one of the two X-ray sources 600a and 600b, or driving the two X-ray sources simultaneously. The controller 799 may be in conjunction with the multi-collimator 781 by being connected thereto. Besides, the controller 799 generates electric signals, which are to be applied to each electrode terminal of the X-ray source, and supplies the electric signals to each connection terminal.

The electrode terminal and connection terminal refer to a conductive electrode terminal and connection terminal, and refer to a structure having a concave or convex shape as well, wherein the electrode terminal corresponds to the connection terminal means that locations, heights, sizes, and shapes thereof are formed to allow the conductive electrode terminal and connection terminal to be electrically connected thereto by contact.

Meanwhile, the main body of the X-ray emission apparatus according to the various embodiments described above may include a power supply, a controller, and the like in common. The power supply may include an internal or external battery, or may include a converter for converting an outer power source into power, which can be used in the apparatus. The power supply may supply a driving voltage having a level and frequency that are required to drive the cartridge-type X-ray source. The controller serves to realize a function of the X-ray emission apparatus by controlling timing, time, or the like that apply the driving voltage directly to the electrode terminals of the cartridge-type X-ray source.

INDUSTRIAL APPLICABILITY

The present invention is relates to a cartridge-type X-ray source and an X-ray emission apparatus using the same, and may be applied to a portable X-ray emission apparatus for intraoral radiography in dental clinics and an X-ray emission apparatus for veterinary radiography or for non-destructive inspection in industrial settings.

The invention claimed is:

1. An X-ray emission apparatus comprising:
   a main body including a cartridge mounting part configured to allow an X-ray source to be replacebley mounted therein,
   wherein the X-ray source generates X-rays onto an X-ray irradiation path, and the X-ray source includes:
      a cathode electrode located at a first end and having a nanostructure to be used as an electron emission source;
      an anode electrode located at a second end having a target surface to emit the X-rays; and
      a housing to secure and insulate the cathode electrode and the anode electrode, and the housing configured to expose a cathode electrode terminal connected to the cathode electrode and an anode electrode terminal connected to the anode electrode to an outside thereof, wherein the cathode electrode terminal and
   the anode electrode terminal differ from each other in at least one of exposure direction, height, size, and shape, and the cartridge mounting part includes first and
   second connection terminals connected with the anode electrode terminal and the cathode electrode terminal, respectively.

2. The X-ray emission apparatus of claim 1, wherein the anode electrode terminal and the cathode electrode terminal are exposed to the outside either toward a same exposure direction or toward a different exposure direction with the height thereof being different from each other.

3. The X-ray emission apparatus of claim 1, wherein each of an outer surface of the housing and the cartridge mounting part is provided with at least one guide member corresponding to each other.

4. The X-ray emission apparatus of claim 1, wherein
   the main body includes a plurality of the cartridge mounting part, wherein each of the plurality of the cartridge mounting part includes the X-ray source mounted therein.

5. The X-ray emission apparatus of claim 4, wherein
   the main body includes a rotary loader to house the plurality of the cartridge mounting part, wherein the rotary loader moves one of the plurality of X-ray sources toward the X-ray irradiation path.

6. The X-ray emission apparatus of claim 4, wherein
   the main body includes a multi-collimator irradiating X-rays generated from at least one of the plurality of X-ray sources onto the X-ray irradiation path.

7. An X-ray source comprising:
   a cathode electrode having a nanostructure to be used as an electron emissions source;
   an anode electrode having a target surface to emit X-rays by electron collision; and
   a housing to secure and insulate the cathode electrode and the anode electrode, and the housing configured to expose a cathode electrode terminal connected to the cathode electrode and an anode electrode terminal connected to the anode electrode to an outside thereof, wherein the cathode electrode terminal and the anode electrode terminal differ from each other in at least one of exposure direction, height, size, and shape,
   wherein the X-ray source is adapted to be replaceably mounted to an X-ray emission apparatus in a cartridge-type manner.

8. The X-ray source of claim 7, wherein
the anode electrode terminal and the cathode electrode terminal are exposed to the outside either toward a same exposure direction or toward a different exposure direction with the height thereof being different from each other.

9. The X-ray source of claim 7, wherein each of an outer surface of the housing and the X-ray emission apparatus is provided with at least one guide member corresponding to each other.

10. The X-ray source of claim 7, wherein the X-ray source further comprising:
a shielding layer; and
a heat conductor.

11. The X-ray source of claim 7, wherein the X-ray source further comprising:
a gate electrode disposed between the cathode electrode and the anode electrode.

12. The X-ray source of claim 11, wherein the X-ray source further comprising:
a focusing electrode disposed between the anode electrode and the gate electrode.

13. The X-ray source of claim 7, wherein the target surface of the anode electrode is sloped.

14. The X-ray emission apparatus of claim 1, wherein the X-ray source further comprising:
a shielding layer; and
a heat conductor.

15. The X-ray emission apparatus of claim 1, wherein the X-ray source further comprising:
a gate electrode disposed between the cathode electrode and the anode electrode.

16. The X-ray emission apparatus of claim 15, wherein the X-ray source further comprising:
a focusing electrode disposed between the anode electrode and the gate electrode.

17. The X-ray emission apparatus of claim 15, wherein the target surface of the anode electrode is sloped.

* * * * *